(12) United States Patent
Zaharchuk

(10) Patent No.: US 12,136,473 B2
(45) Date of Patent: Nov. 5, 2024

(54) METHODS OF PREDICTING DISORDER PROGRESSION FOR CONTROL ARMS WITHIN AN EXPERIMENTAL TRIAL

(71) Applicant: The Board of Trustees of the Leland Stanford Junior University, Stanford, CA (US)

(72) Inventor: Greg Zaharchuk, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 466 days.

(21) Appl. No.: 16/892,158

(22) Filed: Jun. 3, 2020

(65) Prior Publication Data

US 2020/0381096 A1 Dec. 3, 2020

Related U.S. Application Data

(60) Provisional application No. 62/856,653, filed on Jun. 3, 2019.

(51) Int. Cl.
| | |
|---|---|
| *G16H 10/20* | (2018.01) |
| *G06F 18/21* | (2023.01) |
| *G06F 18/25* | (2023.01) |
| *G06N 3/088* | (2023.01) |
| *G06N 20/00* | (2019.01) |

(Continued)

(52) U.S. Cl.
CPC ........... *G16H 10/20* (2018.01); *G06F 18/217* (2023.01); *G06F 18/251* (2023.01); *G06N 3/088* (2013.01); *G06N 20/00* (2019.01); *G06V 10/764* (2022.01); *G06V 10/774* (2022.01); *G06V 10/776* (2022.01); *G06V 10/82* (2022.01); *G16H 10/60* (2018.01); *G16H 20/10* (2018.01);

(Continued)

(58) Field of Classification Search
CPC ........ G16B 40/30; G16H 20/10; G16H 50/50; A61K 51/00; G06F 18/29; G06T 11/008; G06N 5/01
USPC .............................................. 705/3; 600/300
See application file for complete search history.

(56) References Cited

U.S. PATENT DOCUMENTS

| 9,721,340 B2 * | 8/2017 | Gillies .................... G16H 15/00 |
| 10,249,389 B2 * | 4/2019 | Athey .................... G16B 40/30 |

(Continued)

FOREIGN PATENT DOCUMENTS

WO WO-2020028382 A1 * 2/2020 ........... A61B 6/5211

OTHER PUBLICATIONS

Identifying Medical Diagnoses and Treatable Diseases by Image-Based Deep Learning, Daniel S.Kermany et al., article published on Cell 172, 1122-1131, Feb. 22, 2018 (Year: 2018).*

(Continued)

*Primary Examiner* — Dilek B Cobanoglu
(74) *Attorney, Agent, or Firm* — KPPB LLP

(57) ABSTRACT

Methods of performing experimental treatments on a cohort of subjects are provided. A predictive model can be utilized to predict progression of a medical disorder or relevant imaging biomarker. The predicted medical disorder progression can be utilized as a control to determine whether an experimental treatment has an effect on the progression of the medical disorder. In some instances, the enrollment of subjects within a control group for clinical experiment is eliminated or reduced.

19 Claims, 33 Drawing Sheets
(24 of 33 Drawing Sheet(s) Filed in Color)

(51) Int. Cl.

| | |
|---|---|
| *G06V 10/764* | (2022.01) |
| *G06V 10/774* | (2022.01) |
| *G06V 10/776* | (2022.01) |
| *G06V 10/82* | (2022.01) |
| *G16H 10/60* | (2018.01) |
| *G16H 20/10* | (2018.01) |
| *G16H 20/40* | (2018.01) |
| *G16H 30/20* | (2018.01) |
| *G16H 50/30* | (2018.01) |

(52) U.S. Cl.
CPC ............. *G16H 20/40* (2018.01); *G16H 30/20* (2018.01); *G16H 50/30* (2018.01)

(56) References Cited

U.S. PATENT DOCUMENTS

| | | | | |
|---|---|---|---|---|
| 11,798,653 | B2* | 10/2023 | Yu | G06N 5/01 |
| 2007/0038475 | A1* | 2/2007 | Schlessinger | G16H 50/50 705/2 |
| 2010/0280975 | A1* | 11/2010 | Wischik | G16H 50/50 600/300 |
| 2011/0124947 | A1* | 5/2011 | Kuo | A61K 51/00 382/128 |
| 2019/0180153 | A1* | 6/2019 | Buckler | G06F 18/29 |
| 2020/0210767 | A1* | 7/2020 | Do | G06T 11/008 |
| 2020/0258629 | A1* | 8/2020 | Ahmad | G16H 50/20 |
| 2020/0380673 | A1* | 12/2020 | Wang | G06V 10/82 |
| 2022/0223231 | A1 | 7/2022 | Reith et al. | |

OTHER PUBLICATIONS

Google scholar search, Jun. 16, 2022 (Year: 2022).*
Machine Learning in Acute Ischemic Stroke Neuroimaging, Mini Review article, Frontiers in Neurology, Nov. 8, 2018, Sec. Stroke, vol. 9—2018, Haris Kamal, Victor Lopez, Sunil A. Sheth (Year: 2018).*
Abbvie, "Synthetic control arm: the end of the placebos?", printed from https://stories.abbvie.com/stories-synthetic-control-are-end-placebos.htm on Mar. 31, 2021, 9 pgs.
Albers et al., "A multicenter randomized controlled trial of endovascular therapy following imaging evaluation for ischemic stroke (DEFUSE 3)", International Journal of Stroke, Oct. 2017, vol. 12, No. 8, pp. 896-905, published online Mar. 24, 2017, doi: 10.1177/1747493017701147.
Albers et al., "Thrombectomy for Stroke at 6 to 16 Hours with Selection by Perfusion Imaging", The New England Journal of Medicine, Jan. 24, 2018, vol. 378, pp. 708-718, DOI: 10.1056/NEJMoa1713973.
Berkhemer et al., "A randomized trial of intraarterial treatment for acute ischemic stroke", The New England Journal of Medicine, Jan. 1, 2015, vol. 372, No. 1, pp. 11-20, DOI: 10.1056/NEJMoa1411587.
Berry et al., "Creating a synthetic control arm form previous clinical trials: Application to establishing early end points as indicators of overall survival in acute myeloid leukemia (AML)", Journal of Clinical Oncology, May 20, 2017, vol. 35, No. 15_suppl, pp. 7021-7021, published online May 30, 2017, 3 pgs., DOI: 10.1200/JCO.2017.35.15_suppl.7021.
Bivard et al., "Perfusion CT in Acute Stroke: A Comprehensive Analysis of Infarct and Penumbra", Radiology, May 2013, vol. 267. No. 2, pp. 543-550.
Campbell et al., "Endovascular therapy for ischemic stroke with perfusion-imaging selection", The New England Journal of Medicine, Mar. 12, 2015, vol. 372, No. 11. pp. 1009-1018, published online Feb. 11, 2015, doi: 10.1056/NEJMoa1414792.
Chartrand et al., "Deep Learning: A Primer for Radiologists", RadioGraphics, 2017, vol. 37, pp. 2113-2131, https://doi.org/10.1148/rg.201717007.
Davi et al., "Precision Oncology Trials: A Look Ahead", Precision Tools, 2018, pp. 77-83.
Feigin et al., "Global, Regional, and Country-Specific Lifetime Risks of Stroke, 1990 and 2016", The New England Journal of Medicine, 2018, vol. 379, pp. 2429-2437, DOI: 10.1056/NEJMoa1804492.
Goldsack, "Synthetic control arms can save time and money in clinical trials", STAT, Feb. 5, 2019, https://www.statnews.com/2019/02/05/synthetic-control-arms/clinical-trials/, 5 pgs.
Hacke et al., "Thrombolysis with alteplase 3 to 4.5 hours after acute ischemic stroke", The New England Journal of Medicine, Sep. 25, 2008, vol. 359, No. 13, pp. 1317-1329, doi: 10.1056/NEJMoa0804656.
Hyland et al., "Real-Valued (Medical) Time Series Generation with Recurrent Conditional GANs", arXiv:1706.02633v2 [stat.ML], Dec. 4, 2017, 13 pgs.
Inoue et al., "Early Diffusion-Weighted Imaging Reversal After Endovascular Reperfusion Is Typically Transient in Patients Imaged 3 to 6 Hours After Onset", Stroke, Apr. 2014, vol. 45, No. 4, pp. 1024-1028, https://doi.org/10.1161/STROKEAHA.113.002135.
Jia et al., "Generation of "Virtual" Control groups for Single Arm Prostate Cancer Adjuvant Trials", PLOS One, Jan. 21, 2014, vol. 9, No. 1, e85010, pp. 1-11, doi: 10.1371/journal/pone.00855010.
Jonsdottir et al., "Predicting Tissue Outcome from Acute Stroke Magnetic Resonance Imaging", Stroke, Sep. 1, 2009. vol. 40, Issue 9, pp. 3006-3011, https://doi.org/10.1161/STROKEAHA.109.552216.
Lansberg et al., "MRI profile and response to endovascular reperfusion after stroke (DEFUSE 2): a prospective cohort study", Lancet Neurology, Oct. 2012. vol. 11, No. 10), pp. 860-867, published online Sep. 4, 2012, doi: 10.1016/S1474-4422(12)70203-X.
Lao et al., "Leveraging Disease Progression Learning for Medical Image Recognition", arXiv1806.10128v2 [cs/CV], Sep. 1, 2018, 6 pgs.
Ma et al., "Thrombolysis Guided by Perfusion Imaging up to 9 Hours after Onset of Stroke", The New England Journal of Medicine, May 9, 2019, vol. 380, No. 10, pp. 1795-1803, DOI: 10.1056/NEJMoa1813046.
Mazurowski et al., "Deep learning in radiology: an overview of the concepts and a survey of the state of the art", arXiv:1802.08717v1 [cs.CV], Feb. 10, 2018, 27 pgs.
McKinley et al., "Fully automated stroke tissue estimation using random forest classifiers (FASTER)", Journal of Cerebral Blood Flow & Metabolism, Aug. 1, 2017, vol. 37, Issue 8, pp. 2728-2741, published online Jan. 1, 2016, https://doi.org/10.1177/0271678X16674221.
Milana, "Deep Generative Models for Predicting Alzheimer's Disease Progression from MR Data", Thesis, Academic Year 2017-2018, 121 pgs.
Mozaffarian et al., "Heart Disease and Stroke Statistics—2016 Update", Circulation, Jan. 2016, vol. 133, No. 4, pp. e38-e360, https://doi.org/10.1161/CIR.0000000000000350, (presented in two parts).
Nielsen et al., "Prediction of Tissue Outcome and Assessment of Treatment Effect in Acute Ischemic Stroke Using Deep Learning", Stroke, Jun. 2018, vol. 49, No. 6, pp. 1394-1401, published online May 2, 2018, doi: 10.1161/STROKEAHA.117.019740.
Ogata et al., "The effects of alteplase 3 to 6 hours after stroke in the EPITHET-DEFUSE combined dataset: post hoc case-control study", Stroke, Jan. 2013, vol. 44, No. 1, pp. 87-93, published online Dec. 18, 2012, doi: 10.1161/STROKEAHA.112.668301.
Oktay et al., "Attention U-Net: Learning Where to Look for the Pancreas", arXiv:1804.03999 [cs.CV], Apr. 11, 2008, 10 pgs.
Olivot et al., "Optimal Tmax Threshold for Predicting Penumbral Tissue in Acute Stroke", Stroke, Feb. 1, 2009, vol. 40, Issue 2, pp. 469-475, https://doi.org/10.1161/STROKEAHA.108.526954.
Pinto et al., "Stroke Lesion Outcome Prediction Based on MRI Imaging Combined with Clinical Information", Frontiers in Neurology, Dec. 5, 2018, vol. 9, Article 1060, 10 pgs., doi: 10.3389/fneur.2018.01060.
Preston, "Medidata wants to help control your single-arm clinical trials", May 22, 2017, printed from: https://medcitynews.com/2017/05/medidata-control-arm-clinical-trial/, 9 pgs.

(56) References Cited

OTHER PUBLICATIONS

Purushotham et al., "Apparent diffusion coefficient threshold for delineation of ischemic core", International Journal of Stroke, Apr. 2015, vol. 10, No. 3, pp. 348-353, published online Jun. 27, 2013, doi: 10.1111/ijs.120687.

Ronneberger et al., "U-Net: Convolutional Networks for Biomedical Image Segmentation", arXiv, Retrieved from: https://arxiv.org/pdf/1505.04597.pdf, May 18, 2015, 8 pgs.

Saver et al., "Time to Treatment with Endovascular Thrombectomy and Outcomes from Ischemic Stroke: A Meta-analysis", Journal of the American Medical Association, 2016, vol. 316, No. 12, pp. 1279-1288, doi:10.1001/jama.2016.13647.

Sepahvand et al., "CNN Prediction of Future Disease Activity for Multiple Sclerosis Patients from Baseline MRI and Lesion Labels", Springer Link, printed May 28, 2019 from https://link.springer.com/chapter/10.1007/978-3-030-11723-8_6, 7 pgs.

Stier et al., "Deep Learning of Tissue Fate Features in Acute Ischemic Stroke", Proceedings IEEE International Conference on Bioinformatics Biomed, Nov. 2015, pp. 1316-1321, doi: 10.1109/BIBM.2015.7359869.

Welker et al., "ASFNR recommendations for clinical performance of MR dynamic susceptibility contrast perfusion imaging of the brain", American Journal of Neuroradiology, Jun. 2015, vol. 36, pp. E41-E51, http://dx.doi.org/10.3174/ajnr.A4341.

Winzeck et al., "ISLES 2016 and 2017—Benchmarking Ischemic Stroke Lesion Outcome Prediction Based on Multispectral MRI", Frontiers in Neurology, Sep. 13, 2018, vol. 9, Article 679, pp. 1-20, https://doi.org/10.3389/fneur.2018.00679.

World Health Organization, "The top 10 causes of death", WHO Fact Sheet, Dec. 9, 2020, 9 pgs.

Yu et al., "Defining Core and Penumbra in Ischemic Stroke: A Voxel- and Volume-Based Analysis of Whole Brain CT Perfusion", Scientific Reports, Feb. 10, 2016, vol. 6, No. 20932, pp. 1-7, doi: 10.1038/srep20932.

Yu et al., "Use of Deep Learning to Predict Final Ischemic Stroke Lesions from Initial Magnetic Resonance Imaging", JAMA Network Open, Mar. 2020, vol. 3, No. 3, e200772, pp. 1-13, doi: 10.1001/jamanetworkopen.2020.0772.

Brendel et al., "Improved longitudinal [18F]-AV45 amyloid PET by white matter reference and VOI-based partial volume effect correction", NeuroImage, vol. 108, Mar. 2015, pp. 450-459.

Chen et al., "Improved Power for Characterizing Longitudinal Amyloid-β PET Changes and Evaluating Amyloid-Modifying Treatments with a Cerebral White Matter Reference Region", The Journal of Nuclear Medicine, vol. 56, No. 4, Apr. 2015, pp. 560-566.

Choi et al., "Can Arterial Spin-Labeling with Multiple Postlabeling Delays Predict Cerebrovascular Reserve?", American Journal of Neuroradiology, vol. 39, No. 1, Jan. 2018, pp. 84-90.

Choi et al., "Predicting cognitive decline with deep learning of brain metabolism and amyloid imaging", Behavioural Brain Research, vol. 344, May 15, 2018, pp. 103-109.

Ding et al., "A Deep Learning Model to Predict a Diagnosis of Alzheimer Disease by Using 18F-FDG PET of the Brain", Radiology, vol. 290, No. 2, Feb. 2019, Online Publication: Nov. 6, 2018, pp. 456-464.

Hammernik et al., "Learning a Variational Network for Reconstruction of Accelerated MRI Data", Magnetic Resonance in Medicine, vol. 79, No. 6, Jun. 2018, pp. 3055-3071.

Hekler et al., "Pathologist-level classification of histopathological melanoma images with deep neural networks", European Journal of Cancer, vol. 115, Jul. 2019, pp. 79-83.

Landau et al., "Measurement of Longitudinal β-Amyloid Change with 18F-Florbetapir PET and Standardized Uptake Value Ratios", The Journal of Nuclear Medicine, vol. 56, No. 4, Apr. 1, 2015, pp. 567-574.

Liu et al., "Deep Learning MR Imaging-based Attenuation Correction for PET/MR Imaging", Radiology, vol. 286, No. 2, Feb. 2018, pp. 676-684.

Reith et al., "Application of Deep Learning to Predict Standardized Uptake Value Ratio and Amyloid Status on 18F-Florbetapir PET Using ADNI Data", American Journal of Neuroradiology, vol. 41, No. 6, Jun. 1, 2020, 7 pgs.

Singh et al., "Deep Learning based Classification of FDG-PET Data for Alzheimers Disease Categories", Proceedings vol. 10572, 13th International Conference on Medical Information Processing and Analysis; 105720J, Nov. 17, 2017, 15 pgs.

Thamm et al., "Contralateral Hemispheric Cerebral Blood Flow Measured With Arterial Spin Labeling Can Predict Outcome in Acute Stroke", Stroke, vol. 50, No. 12, Dec. 2019, pp. 3408-3415.

Yoo et al., "Deep Learning of Brain Lesion Patterns for Predicting Future Disease Activity in Patients with Early Symptoms of Multiple Sclerosis", Deep Learning and Data Labeling for Medical Applications, Springer International Publishing, Proceedings of the First International Workshop, LABELS 2016, and Second International Workshop, DLMIA 2016, pp. 86-94.

Yun et al., "Monitoring Cerebrovascular Reactivity through the Use of Arterial Spin Labeling in Patients with Moyamoya Disease", Radiology, vol. 278, No. 1, Jan. 2016, pp. 205-213.

Zhu et al., "Image reconstruction by domain-transform manifold learning", Nature, vol. 555, Mar. 22, 2018, pp. 487-492.

\* cited by examiner

Fig. 6

Table 1. Clinical Information on All Patients and Subgroups

| Characteristic | Reperfusion status | | | | |
|---|---|---|---|---|---|
| | All (N = 182) | Minimal (n = 32) | Major (n = 67) | Partial (n = 41) | Unknown (n = 42) |
| Male | 85 (46.7) | 19 (59.4) | 34 (50.7) | 17 (41.5) | 15 (35.7) |
| Age, mean (SD), y | 65 (15) | 62 (15) | 64 (16) | 67 (14) | 64 (17) |
| Hypertension | 126 (69.2) | 26 (81) | 41 (61.2) | 31 (75.6) | 28 (66.7) |
| Diabetes | 44 (24.2) | 8 (25.0) | 13 (19.4) | 12 (29.3) | 11 (26.2) |
| Dyslipidemia | 83 (45.6) | 18 (56.3) | 28 (41.8) | 25 (61.0) | 12 (28.6) |
| Atrial fibrillation | 58 (31.9) | 8 (25.0) | 23 (34.3) | 16 (39.0) | 11 (26.2) |
| Site of occlusion | | | | | |
|   MCA M1 | 86 (59.3) | 10 (43.5) | 38 (62.3) | 21 (60.0) | 17 (63.0) |
|   MCA M2 | 21 (14.5) | 8 (34.8) | 4 (6.6) | 4 (11.4) | 5 (18.5) |
|   MCA M3 | 4 (2.8) | 0 | 2 (3.3) | 2 (5.7) | 1 (3.7) |
|   ICA | 34 (23.4) | 5 (21.7) | 17 (27.9) | 8 (22.9) | 4 (14.8) |
| Treatment methods | | | | | |
|   IV tPA | 101 (55.5) | 17 (53.1) | 36 (53.7) | 22 (53.7) | 26 (61.9) |
|   Thrombectomy | 139 (76.4) | 22 (68.8) | 60 (89.6) | 31 (75.6) | 26 (61.9) |
|   No treatment | 19 (10.4) | 6 (18.8) | 2 (3.0) | 4 (9.8) | 7 (16.7) |
| Onset to treatment time, median (IQR), h | 6.0 (4.6-8.3) | 7.1 (4.7-8.4) | 6.0 (4.6-9.2) | 5.6 (3.8-7.1) | 6.6 (4.9-8.8) |
| Baseline DWI lesion volume, median (IQR), mL | 28 (11-60) | 42 (16-131) | 19 (9-47) | 37 (16-83) | 30 (14-61) |
| Baseline Tmax lesion volume, median (IQR), mL | 116 (67-168) | 105 (56-153) | 111 (69-153) | 156 (80-210) | 123 (82-171) |
| PWI:DWI mismatch ratio, median (IQR) | 3.9 (2.2-9.7) | 2.6 (1.4-4.8) | 5.2 (2.7-12.6) | 3.8 (2.5-7.0) | 3.6 (2.1-8.9) |
| Baseline NIHSS score, median (IQR) | 15.0 (10.0-19.0) | 13.0 (8.5-21.0) | 15.0 (10.0-19.0) | 17.0 (12.0-20.0) | 14.0 (11.0-19.0) |
| Symptomatic hemorrhage | 13 (7.1) | 4 (12.5) | 4 (6.0) | 2 (4.9) | 3 (7.1) |
| Reperfusion rate, median (IQR), % | 74 (29-100) | 0 (0-11) | 100 (96-100) | 56 (43-68) | NA |
| Final infarct volume, median (IQR), mL | 54 (16-117) | 86 (35-257) | 23 (9-64) | 82 (27-163) | 52 (21-109) |
| mRS score at 90 d, median (IQR) | 3 (1-4) | 3 (1-4) | 2 (1-3) | 4 (3-5) | 3 (1-4) |

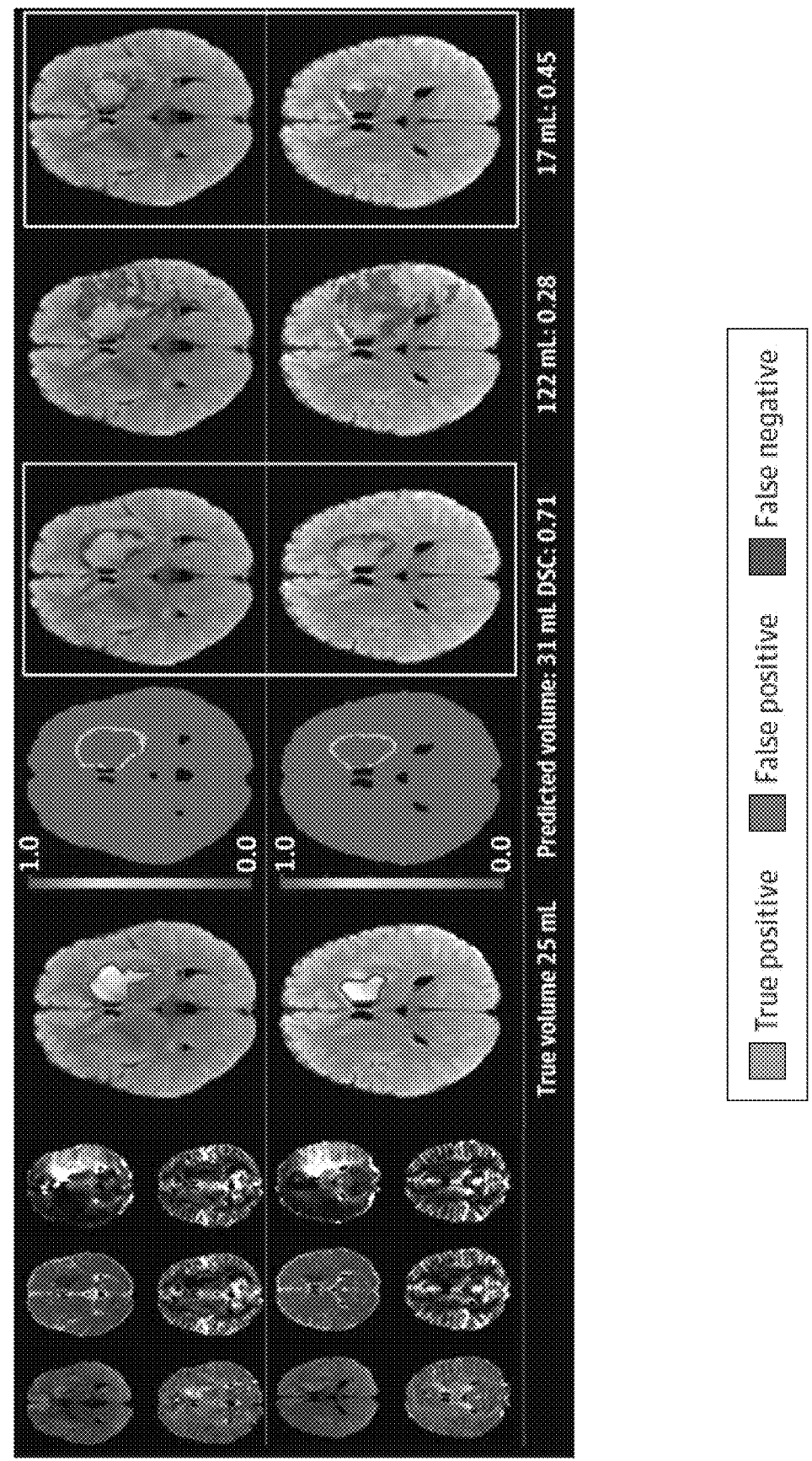

Fig. 11

Table 2. Model Performance and Comparison Between Model and Tmax and ADC Methods

| Perfusion Model | Median (IQR) | | | | | Volume Error, mL | |
|---|---|---|---|---|---|---|---|
| | AUC | DSC | PPV | Sensitivity | Specificity | Lesion | Absolute Lesion |
| Minimal (n = 32) | 0.90 (0.85 to 0.94) | 0.58 (0.31 to 0.67) | 0.71 (0.39 to 0.85) | 0.54 (0.36 to 0.80) | 0.97 (0.95 to 0.99) | −3 (−84 to 18) | 39 (13 to 107) |
| Tmax >6 s plus ADC <620 × 10⁻⁶ mm²/s | 0.80 (0.74 to 0.85) | 0.55 (0.40 to 0.65) | 0.46 (0.33 to 0.81) | 0.57 (0.47 to 0.74) | 0.94 (0.90 to 0.96) | 9 (−72 to 55) | 59 (23 to 100) |
| P value | <.001 | .37 | .002 | .43 | .002 | .04 | .61 |
| Major (n = 67) | 0.93 (0.89 to 0.96) | 0.48 (0.29 to 0.65) | 0.41 (0.21 to 0.64) | 0.74 (0.50 to 0.80) | 0.97 (0.95 to 0.99) | 16 (−3 to 29) | 19 (10 to 33) |
| ADC <620 × 10⁻⁶ mm²/s | 0.71 (0.59 to 0.78) | 0.45 (0.15 to 0.54) | 0.44 (0.13 to 0.72) | 0.42 (0.19 to 0.59) | 0.99 (0.98 to 1) | −8 (−34 to 6) | 12 (7 to 34) |
| P value | <.001 | .002 | .02 | <.001 | <.001 | <.001 | .26 |
| Partial (n = 41) | 0.90 (0.86 to 0.96) | 0.53 (0.36 to 0.68) | 0.59 (0.38 to 0.82) | 0.61 (0.42 to 0.81) | 0.96 (0.92 to 0.98) | 9 (−21 to 37) | 36 (15 to 66) |
| Unknown (n = 42) | 0.92 (0.86 to 0.96) | 0.52 (0.31 to 0.67) | 0.54 (0.33 to 0.76) | 0.60 (0.39 to 0.86) | 0.96 (0.94 to 0.99) | 6 (−11 to 32) | 26 (10 to 38) |

Abbreviations: ADC, apparent diffusion coefficient; AUC, area under the curve; DSC, Dice score coefficient; IQR, interquartile range; PPV, positive predictive value; Tmax, time to maximum of the residue function.

Fig. 13A

Table 3. Summary of MRI acquisition parameters

| | Single-delay ASL | Multidelay ASL (Hadamard encoding) | T1W | T2-FLAIR | Phase-Contrast angiography |
|---|---|---|---|---|---|
| Sequence | 3-D fast spin echo with spiral readout | 3-D fast spin echo with spiral readout | 3-D fast spoiled gradient echo | 2-D spin echo | Cardiac gated fast low-angle gradient echo |
| Repetition time (ms) | 4854 | 6891 | 9.6 | 9500 | 12.4 |
| Echo time (ms) | 10.7 | 22.7 | 3.8 | 140 | 4.6 |
| Inversion time (ms) | - | - | 400 | 2300 | - |
| Flip angle (degree) | - | - | 13 | 111 | 20 |
| Label duration (ms) | 1450 | 1700 | - | - | - |
| Post-label delay (ms) | 2025 | 300, 2000, 3700 (effective post-label delay) | - | - | - |
| In plane resolution | 3.73 | 5.77 | 0.94 | 0.47 | 0.375 |

Fig. 13B

| | | | | | |
|---|---|---|---|---|---|
| (mm) | | | | | |
| Slice thickness (mm) | 4.0 | 4.0 | 1.0 | 5.0 | 3.0 |
| Number of averages | 3 | 2 | 1 | 1 | 2 |
| Encoding velocity (cm/s) | No vascular crushing | 4 | - | - | 100 |
| Spiral number of arms | 8 | 4 | - | - | - |
| Points/arm | 512 | 512 | - | - | - |
| Acquisition time (min) | 4:13 | 4:47 | 3:36 | 2:23 | ~1:30 |

Note.— ASL = arterial spin labeling, T1W = T1 weighted image, T2-FLAIR = T2 weighted fluid-attenuated inversion recovery image.

Fig. 17A

Table 4. Patient Demographics

| Patient # | Sex | Age (y) | Stenosis/occlusion site | Prior Stroke | Prior Bypass |
|---|---|---|---|---|---|
| 1 | M | 30 | Right M1 | - | - |
| 2 | M | 46 | Bilateral A1, Left M1 | Left infarct | Left bypass |
| 3 | F | 53 | Bilateral A1, M1 | - | Bilateral bypass |
| 4 | M | 46 | Bilateral M1 | Right hemorrhage | Bilateral bypass |
| 5 | F | 64 | Bilateral A1, M1 | Left infarct | - |
| 6 | F | 18 | Bilateral A1, Right M1, P1 | Right infarct | - |
| 7 | F | 27 | Left M1 | - | - |
| 8 | F | 29 | Left M1 | - | Left bypass |
| 9 | F | 50 | Bilateral A1, M1 | - | - |
| 10 | F | 44 | Left M1 | Left infarct | Left bypass |
| 11 | F | 38 | Right M1 | - | - |
| 12 | F | 57 | Bilateral A1, M1 | Left infarct | - |
| 13 | F | 51 | Bilateral A1, M1 | Bilateral infarct | Right bypass |
| 14 | F | 36 | Bilateral A1, M1 | Bilateral infarct | - |
| 15 | F | 21 | Bilateral M1, Left A1 | Bilateral infarct | - |

Fig. 17B

| 16 | F | 33 | Bilateral A1, M1 | - | - |
| 17 | F | 60 | Bilateral A1, M1 | - | - |
| 18 | M | 53 | Bilateral A1, Left M1 | - | - |
| 19 | F | 31 | Bilateral A1, M1 | - | - |
| 20 | F | 49 | Left M1, Right A1 | - | - |
| 21 | F | 43 | Right A1, M1 | - | - |
| 22 | M | 32 | Right M1 | Right infarct | - |
| 23 | M | 33 | Left M1 | - | - |
| 24 | M | 32 | Bilateral A1, M1 | - | - |

Summary

| Patients | 17F/7M | 41±12 | 16 Bilateral/8 Unilateral | 10 (41.7%) | 6 (25.0%) |
| HCs | 9F/3M | 39±16 | | - | - |

Note.—A1 = first segment of anterior cerebral artery, M1 = first segment of middle cerebral artery, P1 = first segment of posterior cerebral artery, HCs = healthy controls.

Fig. 19A

Table 5. Image Quality Metrics

Patients with Moyamoya Disease (n = 24)

| | RMSE | | | | PSNR | | | | SSIM | | | |
|---|---|---|---|---|---|---|---|---|---|---|---|---|
| | Mean | STD | Friedman test | Post hoc* | Mean | STD | Friedman test | Post hoc* | Mean | STD | Friedman test | Post hoc* |
| PET-plus-MRI | 0.142 | 0.032 | $p < 0.001$ | [a] $p < 0.001$ | 21.6 | 1.2 | $p < 0.001$ | [a] $p < 0.001$ | 0.590 | 0.073 | $p < 0.001$ | [a] $p < 0.001$ |
| MRI-only | 0.144 | 0.034 | | [b] $p < 0.001$ | 21.5 | 1.4 | | [b] $p < 0.001$ | 0.572 | 0.074 | | [b] $p < 0.001$ |
| ASL-rACBF | 0.370 | 0.205 | | [c] $p = 0.39$ | 14.2 | 4.9 | | [c] $p = 0.39$ | 0.253 | 0.163 | | [c] $p = 0.25$ |

Fig. 19B

Healthy Controls (n = 12)

| Model | RMSE | | | | PSNR | | | | SSIM | | | |
|---|---|---|---|---|---|---|---|---|---|---|---|---|
| | Mean | STD | Friedman test | Post hoc* | Mean | STD | Friedman test | Post hoc* | Mean | STD | Friedman test | Post hoc* |
| PET-plus-MRI | 0.126 | 0.024 | $p < 0.001$ | [a] $p = 0.003$ | 22.9 | 0.7 | $p = 0.005$ | [a] $p < 0.001$ | 0.633 | 0.086 | $p < 0.001$ | [a] $p < 0.001$ |
| MRI-only | 0.136 | 0.017 | | [b] $p = 0.31$ | 22.1 | 0.7 | | [b] $p = 0.10$ | 0.613 | 0.068 | | [b] $p = 0.004$ |
| ASL-rΔCBF | 0.217 | 0.115 | | [c] $p = 0.31$ | 19.0 | 3.9 | | [c] $p = 0.10$ | 0.416 | 0.174 | | [c] $p = 0.10$ |

Note.- ASL-rΔCBF = relative cerebral blood flow change measured by multidelay arterial spin labeling, PSNR = peak signal-to-noise ratio, RMSE = root mean squared error, SSIM = structural similarity index, STD = standard deviation.

* Post hoc test is performed by Dunn's multiple comparison test; [a] indicate PET-plus-MRI versus ASL-rΔCBF, [b] indicate MRI-only versus ASL-rΔCBF.

[c] indicates PET-plus-MRI versus MRI-only.

Fig. 22

Table 6. Diagnostic Performance of Model Predictions

| Threshold | Mean-2STD* | | | Mean-3STD | | | Mean-4STD | | |
|---|---|---|---|---|---|---|---|---|---|
| PET-rΔCBF | 0.890 | | | 0.726 | | | 0.683 | | |
| No. Impaired | 58 (40) | | | 40 (28) | | | 31 (22) | | |
| ROIs (n = 144)[†] | | | | | | | | | |
| | AUC | SEN | SPE | AUC | SEN | SPE | AUC | SEN | SPE |
| PET-plus-MRI[‡] | 0.88 | 41 of 58 (71) | 79 of 86 (92) | 0.95 | 35 of 40 (88) | 97 of 104 (93) | 0.92 | 27 of 31 (87) | 98 of 113 (87) |
| | [0.82, 0.94] | [57, 82] | [84, 97] | [0.90, 0.99] | [73, 96] | [87, 97] | [0.87, 0.98] | [70, 96] | [79, 92] |
| MRI-only[‡] | 0.89 | 45 of 58 (78) | 76 of 86 (88) | 0.95 | 35 of 40 (88) | 93 of 104 (89) | 0.92 | 26 of 31 (84) | 98 of 113 (87) |
| | [0.83, 0.94] | [65, 87] | [80, 94] | [0.91, 0.98] | [73, 96] | [82, 95] | [0.88, 0.97] | [66, 95] | [79, 92] |
| ASL-rΔCBF[‡] | 0.78 | 45 of 58 (78) | 64 of 86 (74) | 0.89 | 33 of 40 (83) | 85 of 104 (82) | 0.88 | 26 of 31 (84) | 87 of 113 (77) |
| | [0.70, 0.86] | [65, 87] | [64, 83] | [0.83, 0.95] | [67, 93] | [73, 89] | [0.81, 0.95] | [66, 95] | [68, 84] |
| DeLong's test[§] | [a]p = 0.03 | | | [a]p = 0.09 | | | [a]p = 0.32 | | |
| | [b]p = 0.04 | | | [b]p = 0.11 | | | [b]p = 0.33 | | |
| | [c]p = 0.75 | | | [c]p = 0.89 | | | [c]p = 0.98 | | |

Note.— STD = standard deviation, rΔCBF = relative cerebral blood flow change, ROI = region of interest, AUC = area under receiver operating characteristic curve, SEN = sensitivity, SPE = specificity, ASL-rΔCBF = relative cerebral blood flow change measured by multidelay ASL.

* Mean – 2STD indicates the threshold value is defined as 2STD below the mean of rΔCBF in healthy controls.

[†] Data in parenthesis is percentage.

[‡] Data in parenthesis is percentage, data in square bracket is 95% confidence interval.

[§] Comparison between AUCs from different methods is performed by DeLong's test. [a] indicate PET-plus-MRI versus ASL-rΔCBF, [b] indicates MRI-only versus ASL-rΔCBF, [c] indicates PET-plus-MRI versus MRI-only.

METHODS OF PREDICTING DISORDER PROGRESSION FOR CONTROL ARMS WITHIN AN EXPERIMENTAL TRIAL

CROSS REFERENCE TO RELATED APPLICATIONS

This application claims priority to U.S. Provisional Application Ser. No. 62/856,653, entitled "Prediction of Acute Ischemic Stroke Lesions from Baseline Magnetic Resonance Imaging with Deep Learning: Comparison with a Clinical Thresholding Method" to Greg Zaharchuk, filed Jun. 3, 2019, which is incorporated herein by reference in its entirety.

TECHNOLOGY FIELD

The invention is generally directed to methods to predict disorder progression for control arms within an experimental trial and applications thereof, including clinical trials.

BACKGROUND

In a typical experimental clinical trial, researchers assign patients to an experimental or control group. For example, in a vaccine trial, one set of patients is given a vaccine and second group of patients is given an inert substance (e.g., placebo). Patients are often randomly assigned. Experimental trials are typically performed double blind, meaning both the doctor administering the treatment and the patient receiving the patient are unaware whether the patient is within the test arm or the control arm. The progression of disorder and/or the ability of the treatment to provide a response is monitored, comparing the results between the test and control arms.

SUMMARY

Many embodiments are directed to methods of performing clinical experimentation. In many of these embodiments, a trained and validated computational model predicts progression of a medical disorder utilizing a subject's baseline images. Many embodiments perform a clinical experiment, such as an experimental treatment, on the subject and utilize the predicted progression as a control.

In an embodiment to perform an experimental treatment on a cohort of subjects, a set of one or more baseline biomedical images is captured from each subject of a cohort of subjects. Each subject of the cohort has a medical disorder that is shared among the subjects. For each subject of the cohort, a trained and validated predictive model and the subject's set of baseline biomedical images are utilized to predict the progression of the subjects disorder. For each subject of the cohort, an experimental treatment is administered to the subject. For each subject of the cohort, a set of one or more experimental biomedical images is captured during or at the end of the treatment. For each subject of the cohort, the ability of the experimental treatment to ameliorate the medical disorder is assessed by comparing the data of the captured experimental biomedical images with the data of the predicted disorder progression.

In another embodiment, the trained and validated predictive model was trained with baseline image data and clinical endpoint data collected from a training cohort of individuals, each individual having the medical disorder.

In yet another embodiment, the clinical endpoint data includes biomedical images acquired at the clinical endpoint.

In a further embodiment, the trained and validated predictive model was trained with biomedical image data acquired during the medical disorder progression.

In still yet another embodiment, the prediction model is further trained with clinical data or genetic data.

In yet a further embodiment, the trained and validated predictive model has been assessed utilizing baseline biomedical images of an assessment cohort of subjects.

In yet an even further embodiment, the trained and validated predictive model incorporates a deep neural network (DNN), a convolutional neural network (CNN), a kernel ridge regression (KRR), or a gradient-boosted random forest technique.

In still yet an even further embodiment, the trained and validated predictive model was trained unsupervised.

In still yet an even further embodiment, the trained and validated predictive model was trained utilizing attention that focus the on specific target structures within the baseline biomedical images.

In still yet an even further embodiment, the medical disorder is a physical condition, a mental condition, or a risk of a physical or mental condition that deviates from the norm.

In still yet an even further embodiment, the collection of predicted disorder progression of each subject of the cohort is utilized as a surrogate for a control arm in a clinical experiment that assesses the ability of the experimental treatment to ameliorate the medical disorder.

In still yet an even further embodiment, the results of the predictive model of each subject of the cohort are utilized as an individualized control for the subject using paired statistical tests.

In still yet an even further embodiment, the results of the predictive model of each subject are statistically combined together to formulate the control arm.

In still yet an even further embodiment, the collection of predicted disorder progression of each subject of the cohort is utilized within a control arm in a clinical experiment that assesses the ability of the experimental treatment to ameliorate the medical disorder, wherein the control arm also includes experimental data of subject receiving a placebo or standard of care alone.

In still yet an even further embodiment, the number of subjects within the control arm is less than 50% of the total number of subjects in the clinical experiment.

In still yet an even further embodiment, the number of subjects within the control arm is 5%, 10%, 15%, 20%, 25%, 30%, 35%, 40%, or 45% of the total number of subjects in the clinical experiment.

In still yet an even further embodiment, the baseline biomedical images are obtained via magnetic resonance imaging (MRI), X-ray, fluoroscopic imaging, computed tomography (CT), ultrasound sonography (US), or positron emission tomography (PET).

In still yet an even further embodiment, voxels within each of the baseline biomedical images are weighted relative to other voxels within its image.

In still yet an even further embodiment, the predictive model predicts a clinical endpoint.

In still yet an even further embodiment, the predictive model predicts at least one biomedical image depicting medical disorder progression.

In still yet an even further embodiment, the predictive model predicts the presence at least one biomarker indicating medical disorder progression.

In still yet an even further embodiment, the treatment is administration of a drug.

In still yet an even further embodiment, the treatment is performing a surgical procedure.

In still yet an even further embodiment, the treatment is implanting a prosthetic implant.

In still yet an even further embodiment, the treatment is administration of a vaccine.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The description and claims will be more fully understood with reference to the following figures and data graphs, which are presented as exemplary embodiments of the invention and should not be construed as a complete recitation of the scope of the invention.

FIG. 6 provides a data table of clinical information utilized within a training model, utilized in accordance with an embodiment of the invention.

FIGS. 9A to 9C and 10A to 10C each provide predicted images and actual images of patients with varying levels of reperfusion, generated in accordance with an embodiment of the invention.

FIG. 11 provides a data table of predictive model results compared with Tmax and ADC methods, generated in accordance with an embodiment of the invention.

FIGS. 13A and 13B provide a data table of MRI acquisition parameters, utilized in accordance with an embodiment of the invention.

FIGS. 17A and 17B provides a data table of patient demographics utilized to train a convolutional neural network to predict cerebrovascular reserve, utilized in accordance with an embodiment of the invention.

FIGS. 19A and 19B provide a data table of image quality metrics, utilized in accordance with an embodiment of the invention.

FIG. 22 provides a data table of diagnostic performance results of predictive models, generated in accordance with an embodiment of the invention.

DETAILED DESCRIPTION

Turning now to the drawings and data, various methods for generating deep learning computational models for predicting medical disorder progression and their use within clinical experiments, in accordance with various embodiments, are provided. Some embodiments are directed towards utilizing medical imaging data to train a deep learning computational model to predict disorder progression based on a single or few baseline images. In some embodiments, the trained computational model is then utilized to as a surrogate for a control arm of a clinical experiment. Accordingly, in some embodiments, subjects of a clinical experiment have their baseline images recorded, which is then used within a trained deep computational model to predict how their disorder would progress without intervention; the subjects, however, are administered an experimental treatment and the disorder progression with the treatment intervention is monitored via medical imaging; and the computationally predicted disorder progression without intervention is used as a control to provide a comparison with the amelioration/progression of the disorder of the treated individual.

Prediction of Medical Disorder Progression

A number of embodiments are directed to predicting medical disorder progression from a set of one or more baseline images. A medical disorder is to be understood to be any physical or mental condition or risk of a physical or a mental condition that can be medically assessed. In some embodiments, a medical disorder is a deviation of a physical or a mental condition from the norm, which can often result in a physical or mental ailment.

In some embodiments, a deep learning computational model is utilized to predict progression of a medical disorder. Any appropriate machine learning model can be utilized, including (but not limited to) deep neural networks (DNN), convolutional neural networks (CNN), kernel ridge regression (KRR), and gradient-boosted random forest techniques. Likewise, any appropriate model architecture can be utilized that provides an ability to predict disorder progression. In some embodiments, a CNN is utilized as there is no requirement to define relevant features but are learned from the data sets used for training. In some embodiments, model architectures include hidden layers for nonlinear processing and extraction of important features. In some embodiments, the deep CNN U-net is utilized, which may provide high computational efficiency, sensitivity, and accuracy for segmentation tasks in biomedical image processing (for more on U-net, see O. Ronneberger, P. Fischer, and T. Brox *arXiv:*1505.04597v1 [cs.CV] (2015), the disclosure of which is incorporated herein by reference). Examples of disorder related predictive models are provided within the Exemplary Embodiments section.

Figure 1:
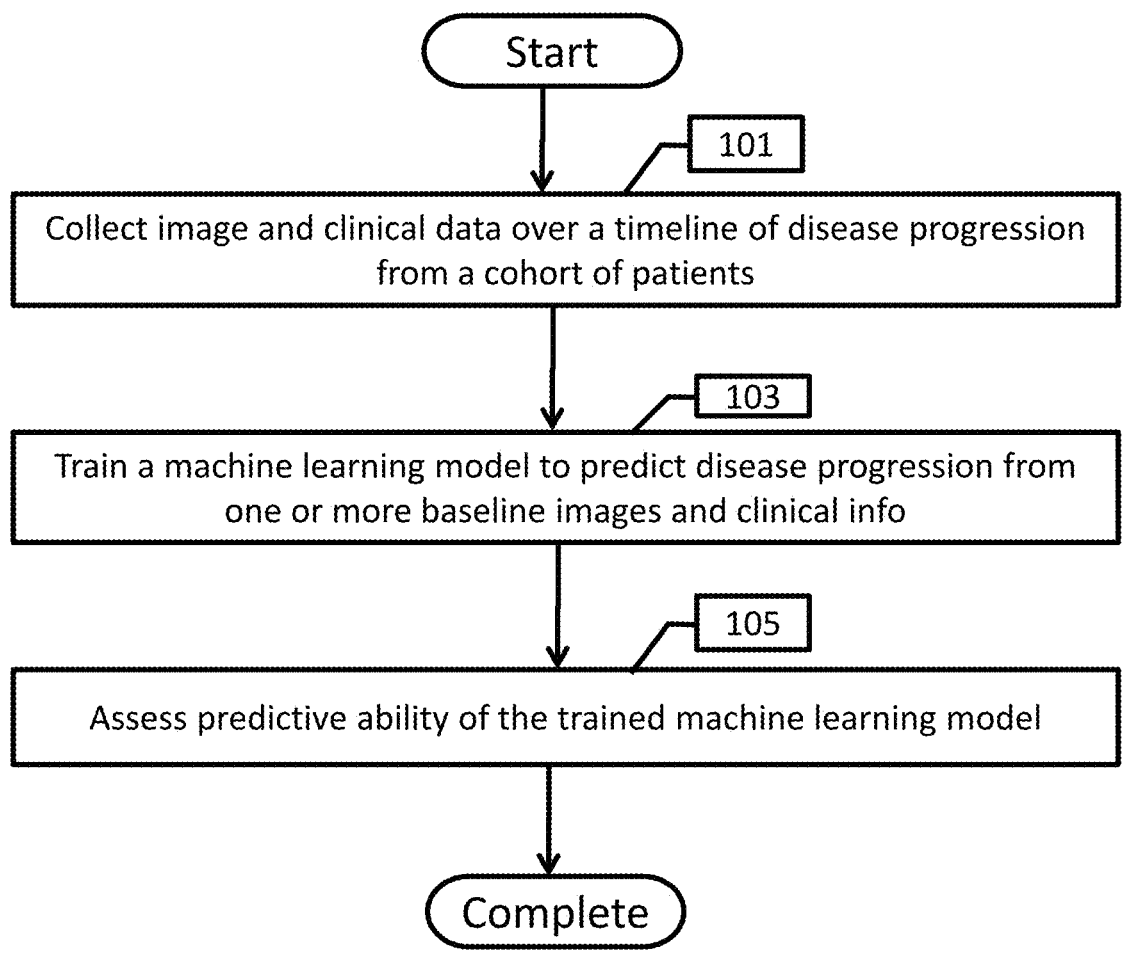
FIG. 1 provides a flow diagram of a method to train a machine learning for predicting disease progression from a baseline image in accordance with various embodiment of the inventions.

Provided in FIG. 1 is a method to build, train, and assess a predictive model that predicts progression of a medical disorder in accordance with various embodiments. Process 200 begins with collecting (201) medical image data of a cohort of patients having a medical similarity (e.g., medical disorder). Typically, the disorder to be modelled progresses in a manner that is assessable via medical imaging. In other words, the progress of any physical or mental condition that can be monitored via medical imaging can be modelled. Examples of risks and/or disorders that can be monitored via medical imaging include (but are not limited to) ischemic stroke, neurodegenerative diseases (e.g., Parkinson's disease, Alzheimer's disease), multiple sclerosis, pneumonia, and cancer/neoplasm tumor growth.

Any appropriate medical image data can be utilized that provides analysis of disorder progress. Likewise, any appropriate imaging modality may be utilized, as appropriate for the disorder being monitored. Examples of medical imaging modalities include (but are not limited to) magnetic resonance imaging (MRI), X-ray, fluoroscopic imaging, computed tomography (CT), ultrasound sonography (US), and positron emission tomography (PET). Various imaging modalities can be combined, such as PET-CT scanning. Likewise, various image data derived from multiple modalities can be collected and be utilized as training data. Further, any appropriate image data can be derived from the collected images and utilized as training data. Images can be acquired by any appropriate means for the disorder to be monitored, including various contrasting methods. Likewise, images can be processed as appropriate. In some embodiments, collected images are normalized between patients within the cohort.

In some embodiments, images are collected from each patient of the cohort over an appropriate period of time. In some embodiments, a baseline image is collected, which is the image collected for the individual. In some embodiments, images are collected at specific time intervals. In some embodiments, images are collected at specific disorder events. In some embodiments, images are collected until a predesignated endpoint. In some embodiments, images are collected until a medical or terminal event.

As depicted in FIG. 1, a machine learning model is trained (103) to predict disorder progression from a set of one or more baseline images. In some embodiments, a model is utilized to predict a specific outcome. In some embodiments, a model is trained with and used to predict the probability of an image or biomarker. In some embodiments, a model is trained with and used to predict the probability of a clinical endpoint. In some embodiments, various models (e.g., biomarker prediction, clinical endpoint) are combined, yielding an overarching assessment.

In some embodiments, a prediction model is trained utilizing biomedical image data. In some embodiments, a prediction model is trained utilizing biomedical image data acquired at a clinical endpoint. In some embodiments, a prediction model is trained utilizing biomedical image data acquired during the progression of the medical disorder (e.g., between the baseline image acquisition and clinical endpoint). In some embodiments, a prediction model is further trained with clinical data, genetic data, or other biomedical data that is relevant to the progression of the medical disorder order.

Any appropriate machine learning model or combination of learning models can be utilized, including (but not limited to) deep neural networks (DNN), convolutional neural networks (CNN), kernel ridge regression (KRR), and/or gradient-boosted random forest decision trees. Likewise, any appropriate model architecture can be utilized that provides an ability to predict disorder progression. In some embodiments, no supervision is provided to train the model. In some embodiments, attention gates are utilized to focus the model to train specific target structures within the collected images. In some embodiments, image voxels are weighted (e.g., positive and negative voxels relative to each other) to provide comparison between patients in the cohort.

In some embodiments, cross-validation is performed. Accordingly, image data can be divided into a number of sets (e.g., 3, 4, 5, 10 sets). A number of sets can be used for training, a number of sets can be used for validation, and number of sets can be used for testing. In some embodiments, the best models for each training set is selected based on the performance of the model on the validation set. In some embodiments, models derived from the training cohorts are cross-validated with each other and/or with validation cohorts. In some embodiments, validated models are combined, averaged, and/or weighted. In some embodiments, each trained model is evaluated on a testing set. In some embodiments, a trained model is to be used to predict disorder progression on individual patients. In some embodiments, a trained model is used to predict collective disorder progression on a cohort of patients.

Process 100 also assesses (105) the predictive ability of the trained machine learning model. Accordingly, in some embodiments, trained models are evaluated for their predictive performance utilizing baseline image data of a cohort of subjects. In some embodiments, the baseline image data of the assessment cohort was not utilized in training or validating the model. To assess prediction, in some embodiments, area under the curve (AUC) is calculated for a trained model. In some embodiments, the output probability threshold for classifying particular voxels as positive or negative is varied to achieve the best prediction. In some embodiments, a Dice score coefficient, which reflects the amount of image overlap between the prediction output and the truth, is utilized. In various embodiments, positive predictive value (PPV), sensitivity, specificity, and/or error is calculated. In some embodiments, models that provide a robust predictive ability as determined by assessments performed can be utilized in a downstream application. In some embodiments, a predictive model is utilized to as a surrogate for a control arm in a clinical experiment.

While specific examples of processes for training and assessing a predictive model utilizing biomedical images are described above, one of ordinary skill in the art can appreciate that various steps of the process can be performed in different orders and that certain steps may be optional according to some embodiments of the invention. As such, it should be clear that the various steps of the process could be used as appropriate to the requirements of specific applications. Furthermore, any of a variety of processes for training and assessing a predictive model appropriate to the requirements of a given application can be utilized in accordance with various embodiments of the invention.

Predictive Models as Surrogates for Control Arms

Various embodiments are directed toward methods of utilizing a trained and validated predictive model as surrogate for a control arm in a clinical experiment. In a traditional clinical experiment, subjects are place within either a test arm that receives a treatment or a control arm that receives a placebo or the standard of care. Various embodiments described herein, on the other hand, utilize a trained predictive model in lieu of or in addition to a traditional control arm. Accordingly, in some embodiments, subjects within a clinical experiment will have a set of one or more baseline biomedical images recorded and their disorder progress predicted utilizing a machine learning model. In some embodiments, the subjects will additionally be treated with the experimental treatment (i.e., traditional treatment arm) and have the results of their treatment will be compared with the predicted results from the machine learning model.

By utilizing a predictive model as a surrogate for a control arm, it eliminates or reduces the need to assign subjects to a control arm. Thus, most or all the subjects of the experiment will receive the experimental treatment, which is desirable to reduce the number of subjects receiving placebo or standard of care alone. Further, surrogate predictive models can be reutilized in numerous clinical experiments for the same disorder, reducing the number of subjects necessary for a control arm in each clinical experiment. With a reduced requirement for subject in a control arm, potential subjects will likely have an increased incentive to participate in an experimental treatment if they know their likelihood of getting the experimental treatment, as opposed to a placebo or stand of care, is greater than fifty percent. Accordingly, surrogate predictive models reduce the number of participants necessary for a study and increase the likelihood that a potential subject will participate.

Figure 2:
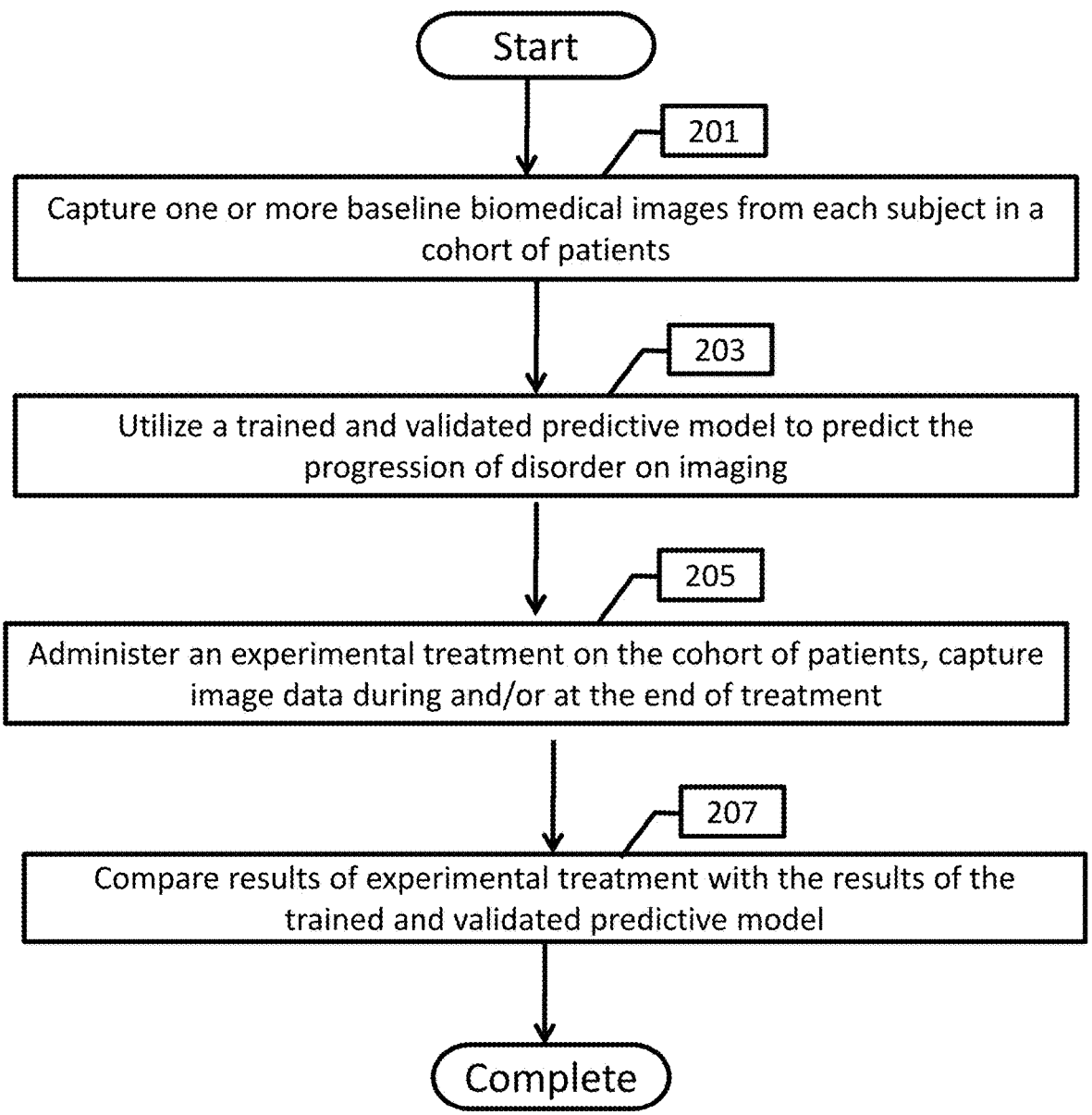
FIG. 2 provides a flow diagram of a method to perform a clinical experiment utilizing a trained and validated predictive model as a control in accordance with various embodiments of the invention.

Provided in FIG. 2 is a method for administering a clinical experiment for a treatment of a medical disorder, where the control arm includes utilizing a trained and validated predictive model, in accordance with various embodiments. Experimental designs can vary but will include an experimental treatment arm having a number of subjects. In some embodiments, a predictive model is utilized in lieu of a control arm having a number of subjects. In some embodiments, a predictive model is utilized to reduce the number of subjects in control arm. Accordingly, in various embodiments, a control arm will have 0% to <50% of the total number of subjects in a clinical experiment. In various embodiments, a control arm will 5%, 10%, 15%, 20%, 25%, 30%, 35%, 40%, or 45% of total subjects.

Process 200 begins by obtaining (201) a set of one or more baseline biomedical images from each subject of a cohort of patients. Any type of baseline biomedical images can be obtained as consistent with the disorder pathology and the type of baseline biomedical images utilized in the trained and validated predictive model. Accordingly, baseline biomedical images can be obtained utilizing MRI, X-ray, CT, US, PET.

For each subject within the cohort of patients, the obtained set of baseline biomedical images is utilized (203) within the trained and validated predictive model to predict the progression of the disorder from the baseline for each subject within the cohort. Any appropriate trained and validated predictive model or combination of predictive models can be utilized including (but not limited to) deep neural networks (DNN), convolutional neural networks (CNN), kernel ridge regression (KRR), and/or gradient-boosted random forest decision trees. In some embodiments, attention gates are utilized to focus the model to train specific target structures within the collected images. In some embodiments, image voxels are weighted (e.g., positive and negative voxels relative to each other) to provide comparison between patients in the cohort. In some embodiments, a model is trained and validated as shown in FIG. 1 and described in the accompanying text.

In some embodiments, utilizing the trained model, a disorder progression prediction is generated for each subject in the cohort. In some embodiments, the model predicts an image or biomarker. In some embodiments, the model predicts the probability of a clinical endpoint. In some embodiments, various models (e.g., biomarker prediction, clinical endpoint) are combined, yielding an overarching assessment.

In addition to predicting the progression of each subject's disorder, an experimental treatment is administered (205) to each subject of the cohort of patients. Any appropriate experimental treatment to be assessed can be administered. In some embodiments, the treatment is a drug (e.g., small molecule or biologic). In some embodiments, the treatment is a surgical procedure. In some embodiments, the treatment is a prosthetic implant. In some embodiments, the treatment is a vaccine.

To evaluate the experimental treatment, a set of biomedical images is captured and collected. In some embodiments, biomedical images are captured and collected along the treatment process. In some embodiments, biomedical images are captured and collected at the end of the treatment process.

Process 200 also compares (207) the results of the experimental treatment with the results of the trained and validated predictive model. In some embodiments, the results of the predictive model are utilized as an individualized control for each subject of the cohort (e.g., using one or more paired statistical tests). In some embodiments, the results of each subject's predictive model within the cohort is combined together to formulate a control arm. In some embodiments, the results of each subject's predictive model within the cohort is combined together and further combined with the subjects that received placebo and/or standard of care to formulate a control arm. Statistical methods can be utilized to determine whether experimental treatment provided an ameliorative effect.

EXEMPLARY EMBODIMENTS

The embodiments of the invention will be better understood with the various examples provided within. Described here are examples of how to predict disorder progression in ischemic stroke using MRI and to predict cerebrovascular reserve using MRI in lieu of a traditional clinical test using a vasodilator drug treatment and PET scan. Prediction of disorder outcome is useful in various applications, such as (for example) a control arm in a clinical experiment.

Example 1

Use of Deep Learning to Predict Final Ischemic Stroke Lesions from Initial Magnetic Resonance Imaging Stroke is a leading cause of mortality and disability worldwide, with approximately 25% lifetime risk globally. Reperfusion therapies, such as intravenous tissue plasminogen activator (IV-tPA) and thrombectomy, are the only effective treatments to reverse the ischemic changes. Time was initially considered to be the single key factor in acute stroke treatment triaging. More recently, clinical trials such as the DEFUSE trials (see T. Ogata, et al., *Stroke; a journal of cerebral circulation*. 2013; 44(1):87-93; M. G. Lansberg, et al., *The Lancet Neurology*. 2012; 11(10):860-867; and G. W. Albers, et al., *The New England journal of medicine*. 2018; 378(8):708-718; the disclosures of which are each incorporated herein by reference) and EXTEND (see H. Ma, et al., *The New England journal of medicine*. 2019; 380(19):1795-1803, the disclosure of which is incorporated herein by reference) have shown the value of identifying viable tissue based on imaging criteria. Therefore, understanding how baseline imaging can indicate tissue fate is important to triage stroke patients appropriately.

Currently, patient selection for endovascular therapy is commonly performed using the diffusion-perfusion mismatch paradigm on the imaging acquired at initial presentation (sometimes called "baseline" imaging). This defines two classes of tissue: the ischemic core, which is presumed to be irreversibly damaged, visualized on diffusion-weighted imaging (DWI) and quantified using the apparent diffusion coefficient (ADC); and the penumbra, which is the region that is at-risk of infarction in the absence of rapid reperfusion, is visualized on perfusion-weighted imaging (PWI) and quantified using the perfusion parameter time-to-maximum of the residue function (Tmax). Clinical trials using simple thresholded values of these imaging parameters have identified thresholds for ADC ($<620\times10^{-6}$ s/mm$^2$) and Tmax ($>6$ sec) and these have been incorporated into clinically available software packages (see G. W. Albers, et al., *International journal of stroke: official journal of the International Stroke Society*. 2017; 12(8):896-905, the disclosure of which is incorporated herein by reference). Despite the simplicity of single-valued thresholds to predict tissue outcome, such approaches can fail to capture the complexity of acute ischemic stroke. While advances have been made to automate the segmentations produced by these software programs, they often still require human interpretation and manual editing to remove non-physiological signals, such as periventricular and contralateral lesions.

Machine learning is a class of computer algorithms that can automatically learn from data without explicit programming. Convolutional neural networks (CNNs) are a subtype of machine learning which do not require humans to define relevant features, instead learning them from data in a training set. Most CNNs use many hidden layers (hence the term 'deep learning') to nonlinearly process and extract important features. Deep learning has shown impressive results on a wide range of computer vision tasks and these are beginning to be applied successfully to medical imaging data. One type of deep CNN architecture known as a U-net has shown much promise for segmentation tasks in medical imaging, due to its high computational efficiency, sensitivity, and accuracy for image segmentation tasks.

In this example, a U-net was used to predict final infarct lesions in acute ischemic stroke patients using the initial MR images as inputs to the model. While the premise of the diffusion-perfusion mismatch is all-or-none reperfusion, such patients only account for a small subgroup of all patients who undergo reperfusion therapy. This severely limits the number of cases available for training. In this example, a model was trained with all available stroke cases and report its performance regardless of reperfusion status. The example provides generalized and individualized prediction for acute ischemic stroke patients.

Materials and Methods

Patient Population: Acute ischemic stroke patients were enrolled from the imaging Collaterals in Acute Stroke (iCAS) study from April 2014 to August 2017 and the Diffusion Weighted Imaging Evaluation for Understanding Stroke Evolution Study-2 (DEFUSE-2) from July 2008 to October 2011; results reported in October 2012. iCAS is an ongoing multi-center observational study enrolling patients with clinical acute ischemic stroke symptoms (≤24 hours from last seen well) attributable to the anterior circulation who were considered for endovascular treatment. Detailed inclusion and exclusion criteria was reported previously (see G. Zaharchuk, et al., *Stroke; a journal of cerebral circulation*. 2015; 46; and T. Thamm, et al., *Stroke; a journal of cerebral circulation*. 2019; 50(12):3408-3415; the disclosures of which are each incorporated herein by reference). The DEFUSE-2 trial enrolled acute ischemic stroke patients within 12 hrs of symptom onset and performed endovascular treatment. The iCAS and DEFUSE-2 study have been approved by the Institutional Review Boards of the participating institutions and informed consent was obtained from all patients.

In this example, patients were excluded if they had: (1) no confirmed anterior circulation stroke on follow-up DWI, (2) no PWI or DWI at arrival, or poor PWI quality, (3) no follow-up T2-weighted fluid-attenuated inversion recovery (T2 FLAIR) images within 3-7 days after stroke onset, or (4) complete reperfusion on baseline PWI (no Tmax >6 sec lesion). More details are in FIG. 3.

Imaging Protocol: Images were acquired at either 1.5 T or 3 T. At presentation, and before reperfusion therapy, all enrolled patients underwent MRI (referred as "baseline"), including DWI (with standard [b=1000 s/mm$^2$] diffusion weighting) and PWI using gadolinium-based contrast agents according to each site's standard protocol. Clinically available post-processing software (RAPID, iSchemiaview, Redwood City, CA) was used to reconstruct perfusion parameter maps including Tmax, mean transit time (MTT), cerebral blood volume (CBV), and cerebral blood flow (CBF). This software also generated ADC segmentation with a threshold of $<620\times10^{-6}$ mm$^2$/s and Tmax segmentation with a threshold of $>6$ sec. Most patients underwent a follow-up PWI study within 24 hrs, which was used to classify patients into minimal, partial, and major reperfusion as described below. T2-FLAIR was obtained 3 to 7 days after stroke onset to determine the final infarct lesion.

Imaging Analysis: The final infarct lesions, which were used as ground truth in this example, were segmented on the T2-FLAIR images by a neuroradiologist blinded to all clinical information. Patients were classified into reperfusion categories based on the 24 hr PWI study using the reperfusion rate:

$$\text{Reperfusion rate} = 100\% \times (1 - [T\max_{24\ hrs} > 6 \text{ sec lesion} / T\max_{baseline} > 6 \text{ sec lesion}])$$

Patients with reperfusion rate ≤20% were classified as minimal reperfusion and patients with reperfusion rate 80% were classified as major reperfusion. Otherwise they were classified as partial reperfusion (if 24 hr PWI images were available) or unknown reperfusion (if not).

Imaging Pre-processing: All images were co-registered and normalized to Montreal Neurological Institute (MNI) template space using SPM12 (Statistical Parametric Mapping, The Wellcome Trust Centre for Neuroimaging, University College London, UK). To compare the model performance in minimal and major reperfusion patients to the current clinical standard-of-care, the Tmax and ADC segmentations from RAPID software were used. Tissue with impaired diffusion (ADC<620×10$^{-6}$ mm$^2$/s) was used to predict the final infarct lesion in major reperfusion patients. For minimal reperfusion patients, where the lesion typically grows to the size of the initial perfusion lesion, the combination of the tissue with impaired diffusion and impaired perfusion (Tmax>6 sec) and ADC<620×10$^{-6}$ mm$^2$/s was used for final infarct prediction.

For input of the deep learning model, DWI, ADC, Tmax, MTT, CBF, CBV were normalized by their mean. To preserve important information from the absolute value of Tmax and ADC, two binary masks were created separately for Tmax>6 sec and ADC<620×10$^{-6}$ mm$^2$/s using simple thresholding.

Figure 4:
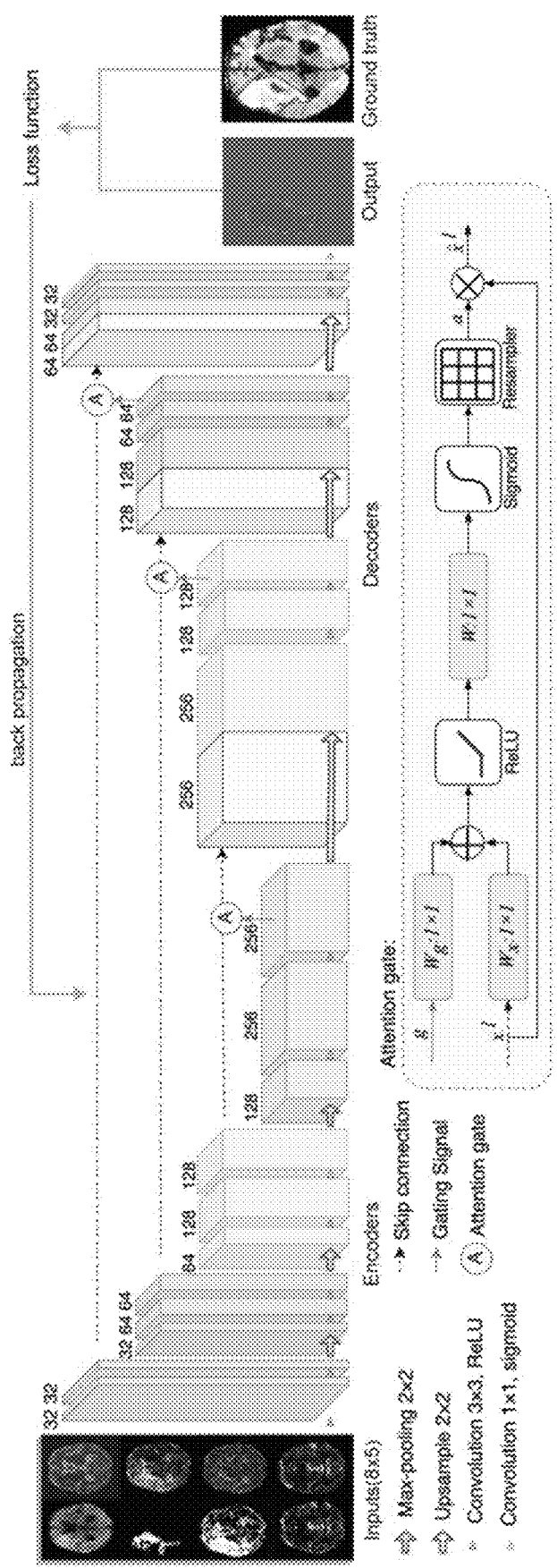
FIG. 4 provides a schema of the architecture of a convolutional neural network to predict ischemic stroke in accordance with an embodiment of the invention.

Neural Network: An attention-gated U-Net architecture was used in this study (See FIG. 4). The traditional U-Net architecture was combined with attention-gates to focus on target structures. A "2.5 D" model is used, meaning that five consecutive slices are used to predict the probabilities of final infarct on the center slice. The ground truth was a binary mask of final infarct lesion of the middle slice measured on the 3-7 day follow-up study. Image mirroring around the midline was used for data augmentation. The model outputs a probability map with voxel values that ranged from 0 to 1. A value close to 1 indicates the voxel is more likely to be inside the infarct lesion, while a value close to 0 indicates the voxel is unlikely to be inside the infarct lesion. Five-fold cross validation was performed.

Performance evaluation: Area-under-curve (AUC) was calculated for both the deep learning models and Tmax and ADC thresholding method. The Dice score coefficient (DSC) reflects the amount of overlap between the prediction and the truth.

DSC=2×True positive/2×True positive+False positive+False negative

Figure 5:
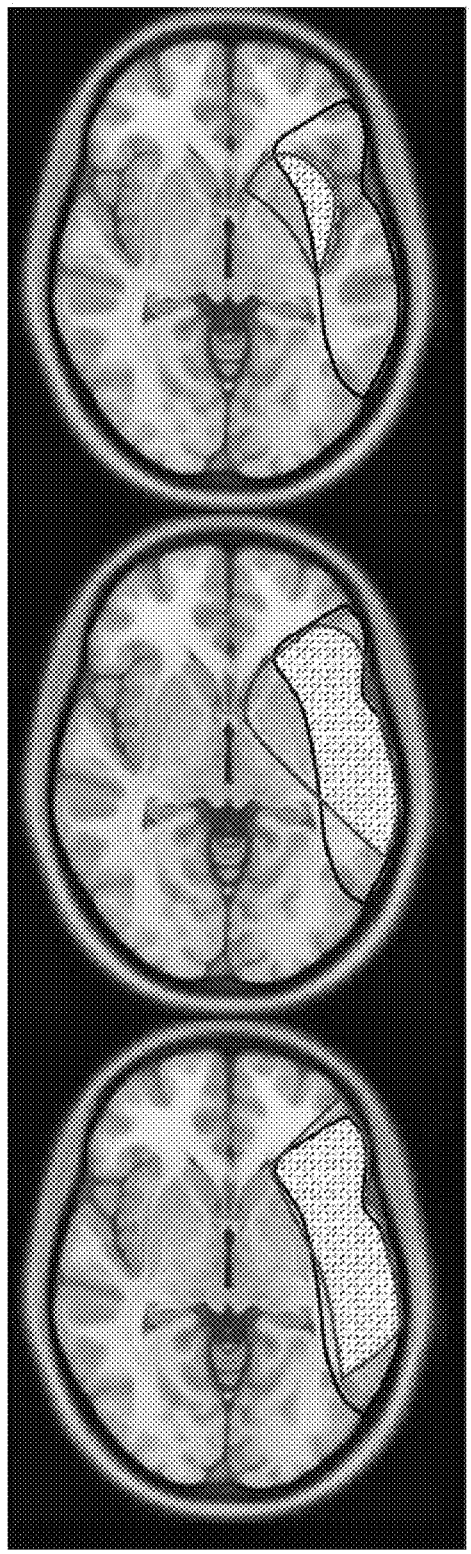
FIG. 5 provides prediction of Dice score coefficient overlaid on top of the true Dice score coefficient, generated in accordance with an embodiment of the invention.

It ranges between 0 and 1, with higher numbers representing more overlap (see FIG. 5 for examples and more information). The DSC is preferred over AUC in tasks where positive and negative samples are significantly imbalanced, as for infarcted voxels in typical stroke patients. It also gives information not just on the predicted size of the lesion, but also on its spatial location, which is important for brain imaging studies.

DSC, positive predictive value (PPV), sensitivity, specificity, and lesion volume error between the prediction and ground truth were calculated for the RAPID Tmax/ADC thresholding methods and the deep learning model with an infarct threshold probability of 0.5. Given that large lesions can bias the lesion volume size predictions without affecting clinical significance, lesion volume predictions was also analyzed in cases with <100 ml lesions separately.

Figure 3:
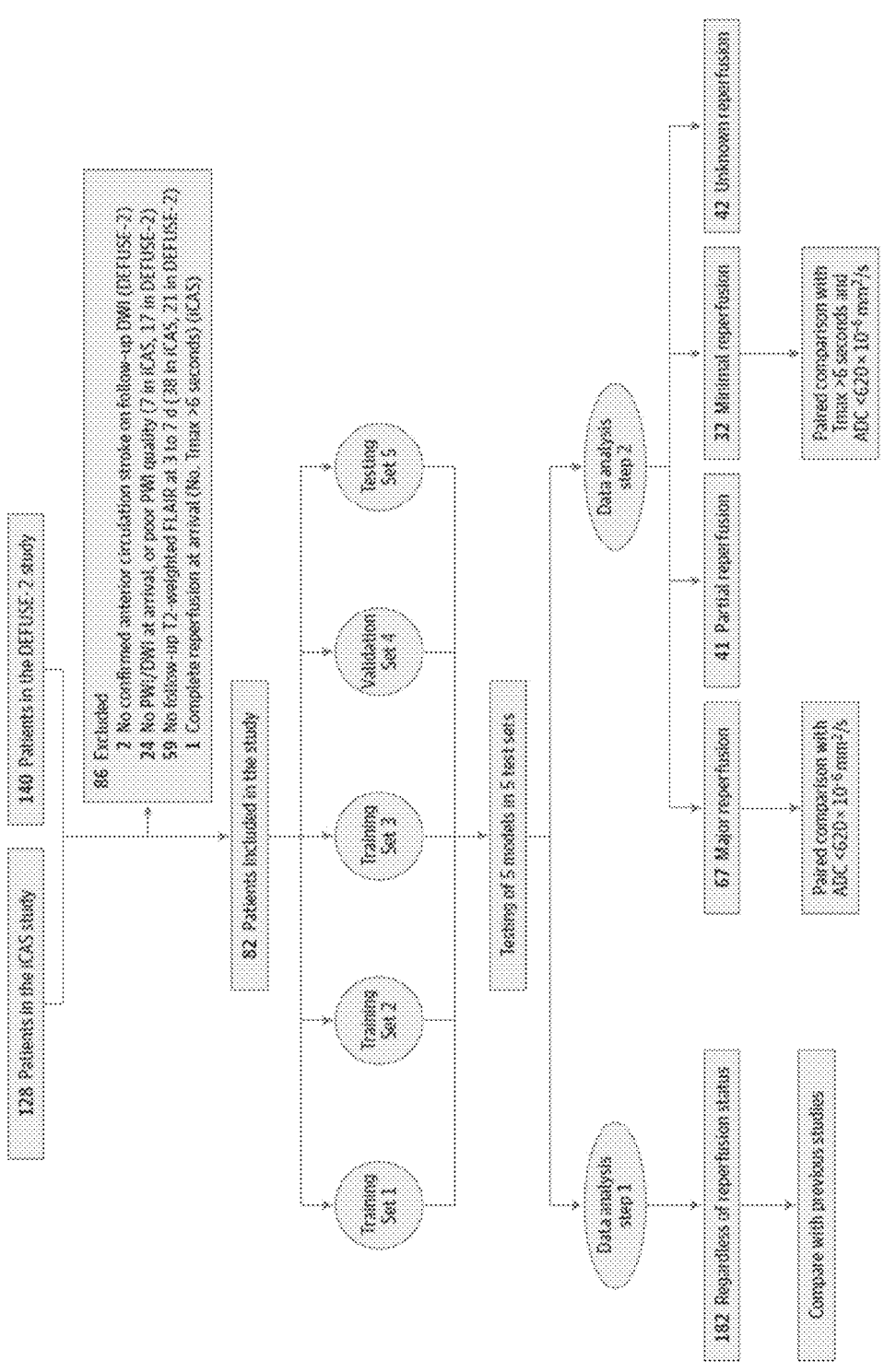
FIG. 3 provides a flow diagram of a method to train a convolutional neural network to predict ischemic stroke in accordance with an embodiment of the invention.

Two data analysis steps were performed (FIG. 3). First, the models were tested on all patients regardless of reperfusion status. Next, the models were tested in major and minimal reperfusion groups to compare with the current clinical threshold-based methods.

Statistical Analysis: Statistical analysis was performed using Stata (version 14.0, Statacorp). Paired-sample Wilcoxon tests were performed to compare AUC, DSC, PPV, sensitivity, specificity, lesion volume error, and absolute lesion volume error between the deep learning and the thresholding methods. Concordance correlation coefficient ($\rho_c$) and Bland-Altman plots were used to analyze the lesion volume predictions. Since infarct sizes were not normally distributed, cubic root transformation was performed for the $\rho_c$ calculation. The correlation was considered excellent when $\rho_c$>0.70, moderate when $\rho_c$ between 0.50 to 0.70, and low when $\rho_c$<0.50[27]. All tests were two-sided and the significance level was adjusted to p<0.003 due to multiple comparisons using Bonferroni correction.

Results

Two hundred sixty eight (268) patients in ICAS and DEFUSE 2 study were reviewed and included 182 patients in the study (FIG. 3). Thirty-two minimal reperfusion patients, 41 partial reperfusion patients, 67 major reperfusion patients, and 42 patients with unknown reperfusion were identified. Their clinical information is summarized in Table 1 (FIG. 6). Major reperfusion patients had fewer M2 occlusions (7% vs 33%), smaller baseline DWI lesions (19 ml IQR 9, 47 vs 42 ml IQR 16, 131), and larger mismatch ratios (5.2 IQR 2.7, 12.6 vs 2.6 IQR 1.4, 4.8) than the minimal reperfusion patients.

Figure 7:
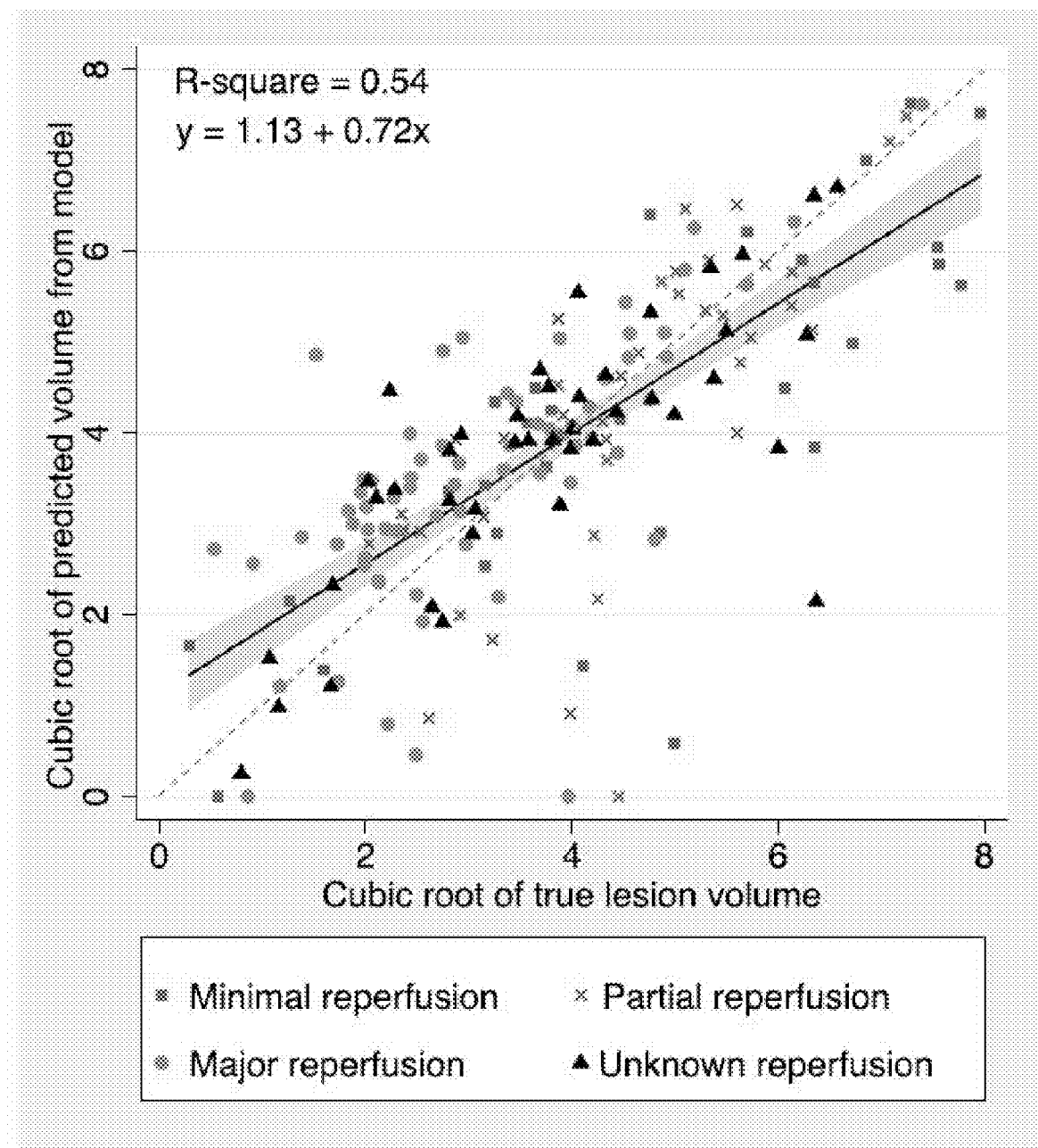
FIGS. 7 and 8 each provide comparison of predicted lesion volume with true lesion model, generated in accordance with an embodiment of the invention.
Figure 8:
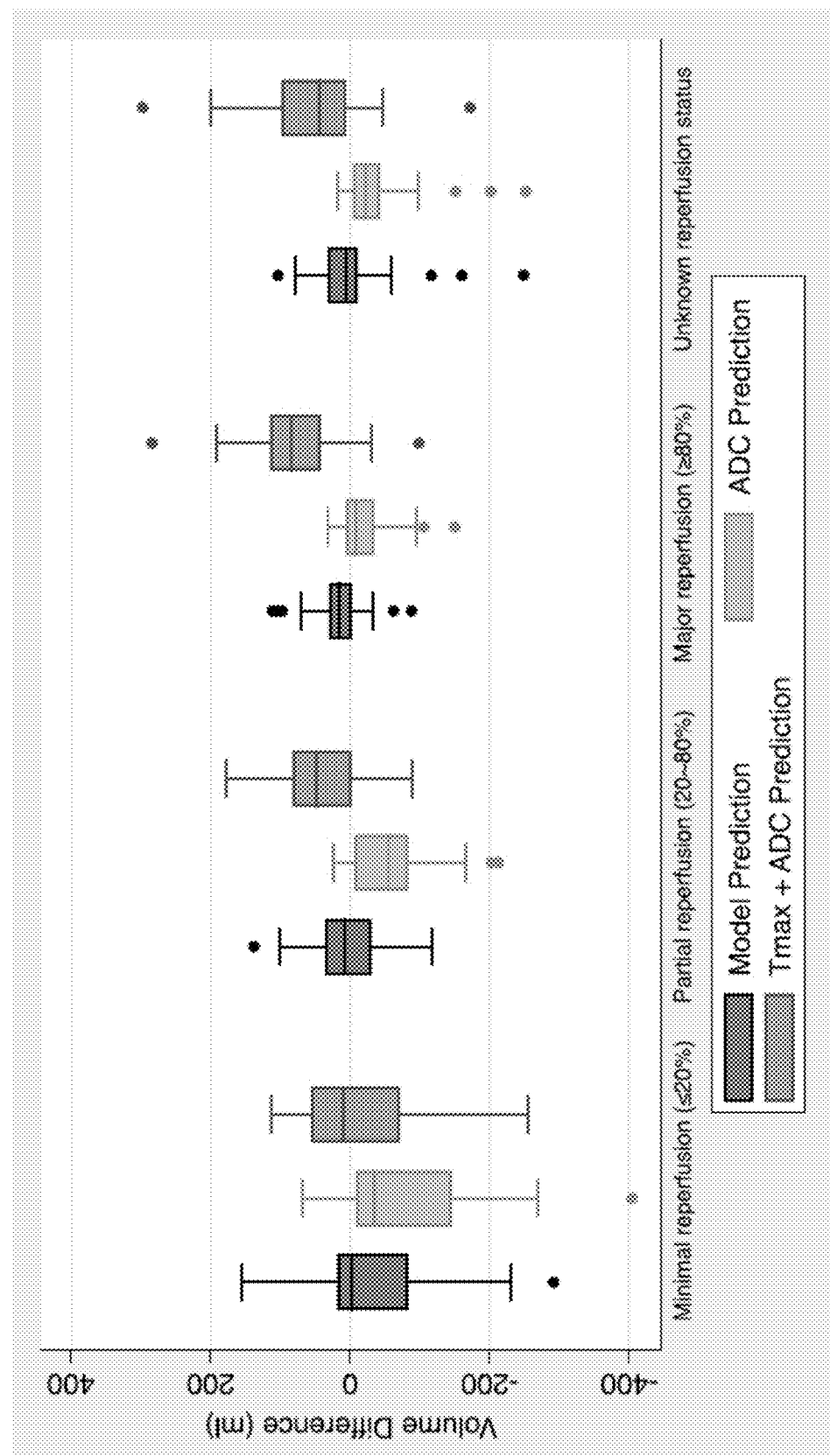
Figure 9A:
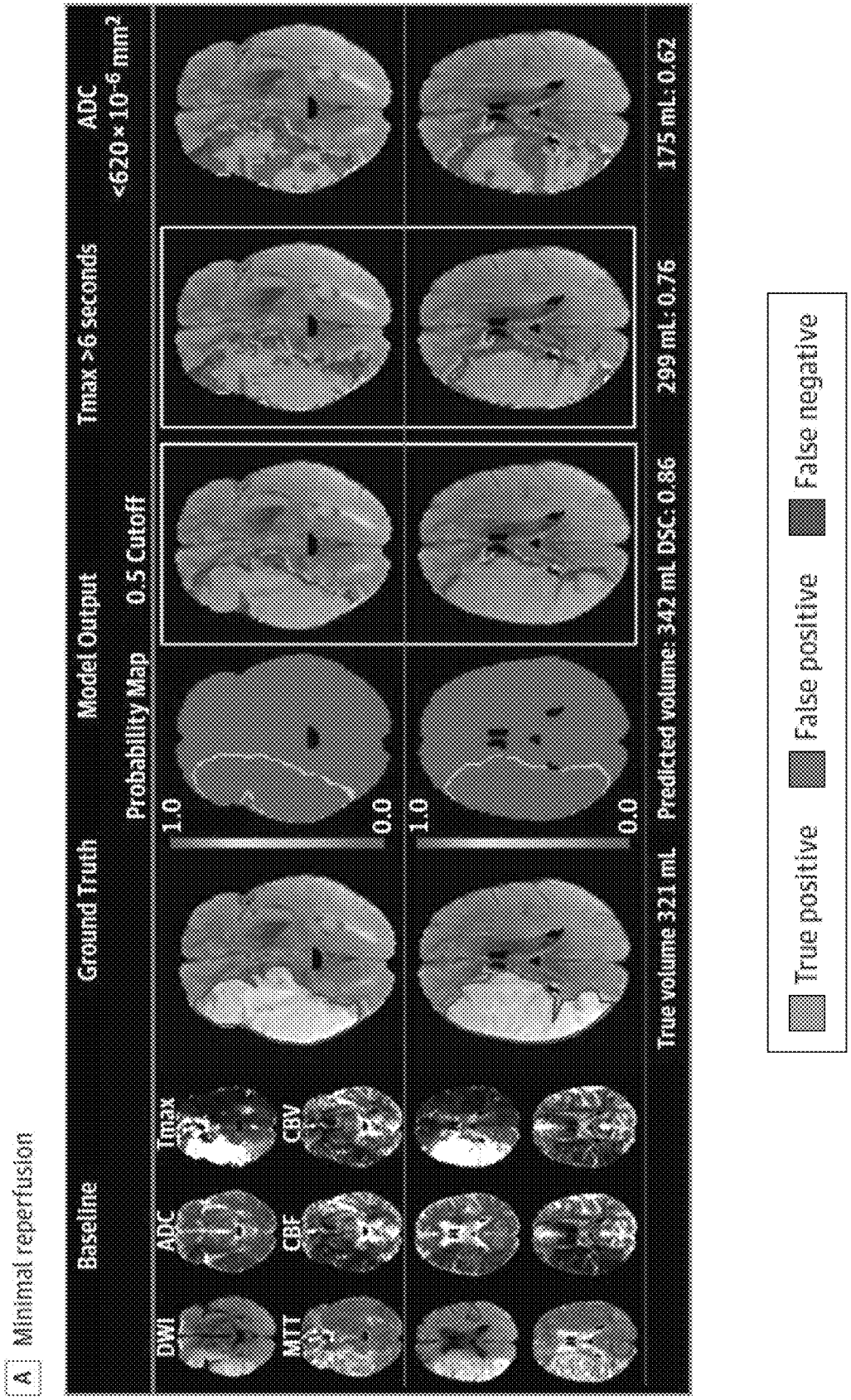
Figure 9C:
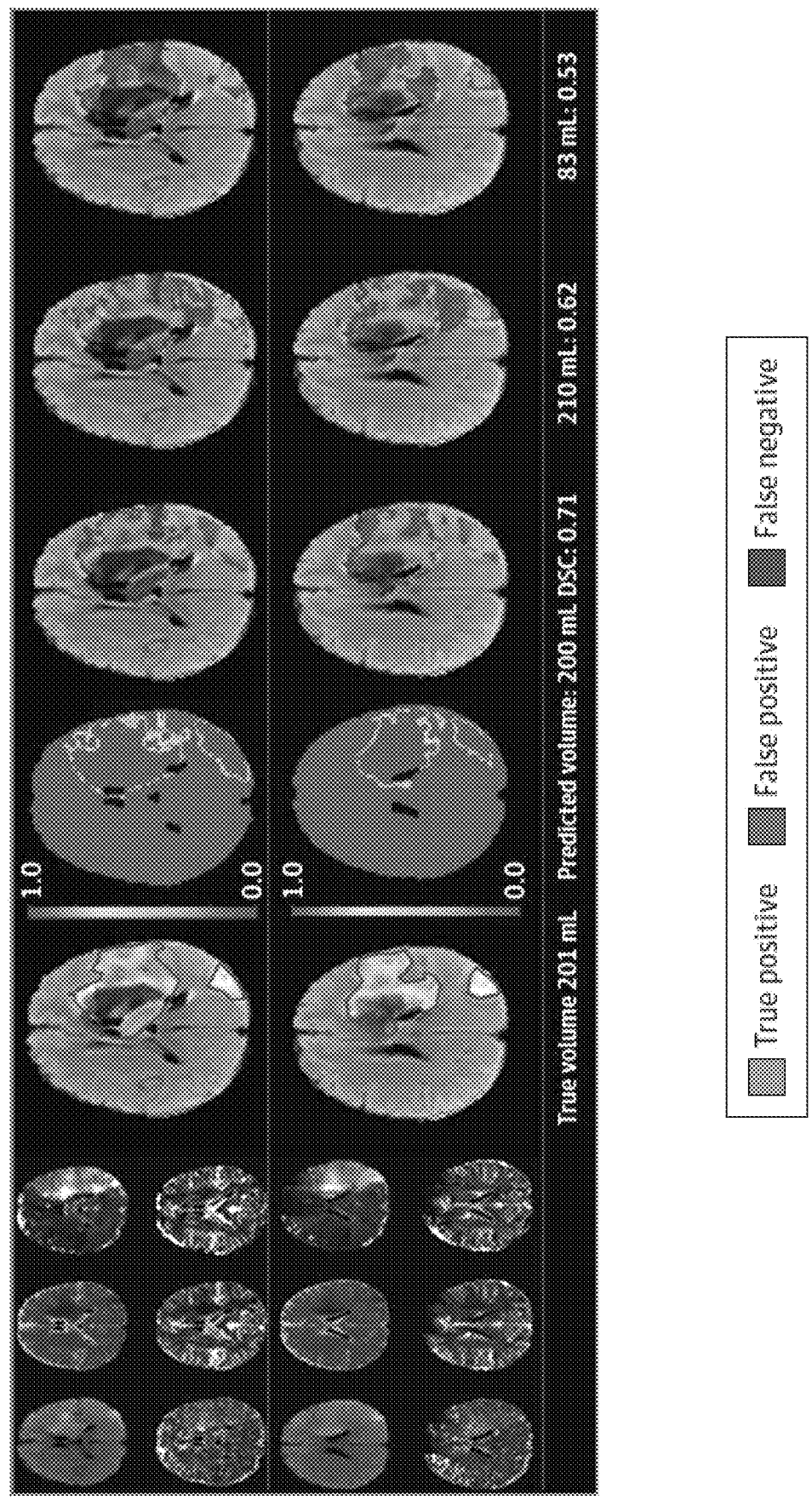
Figure 10A:
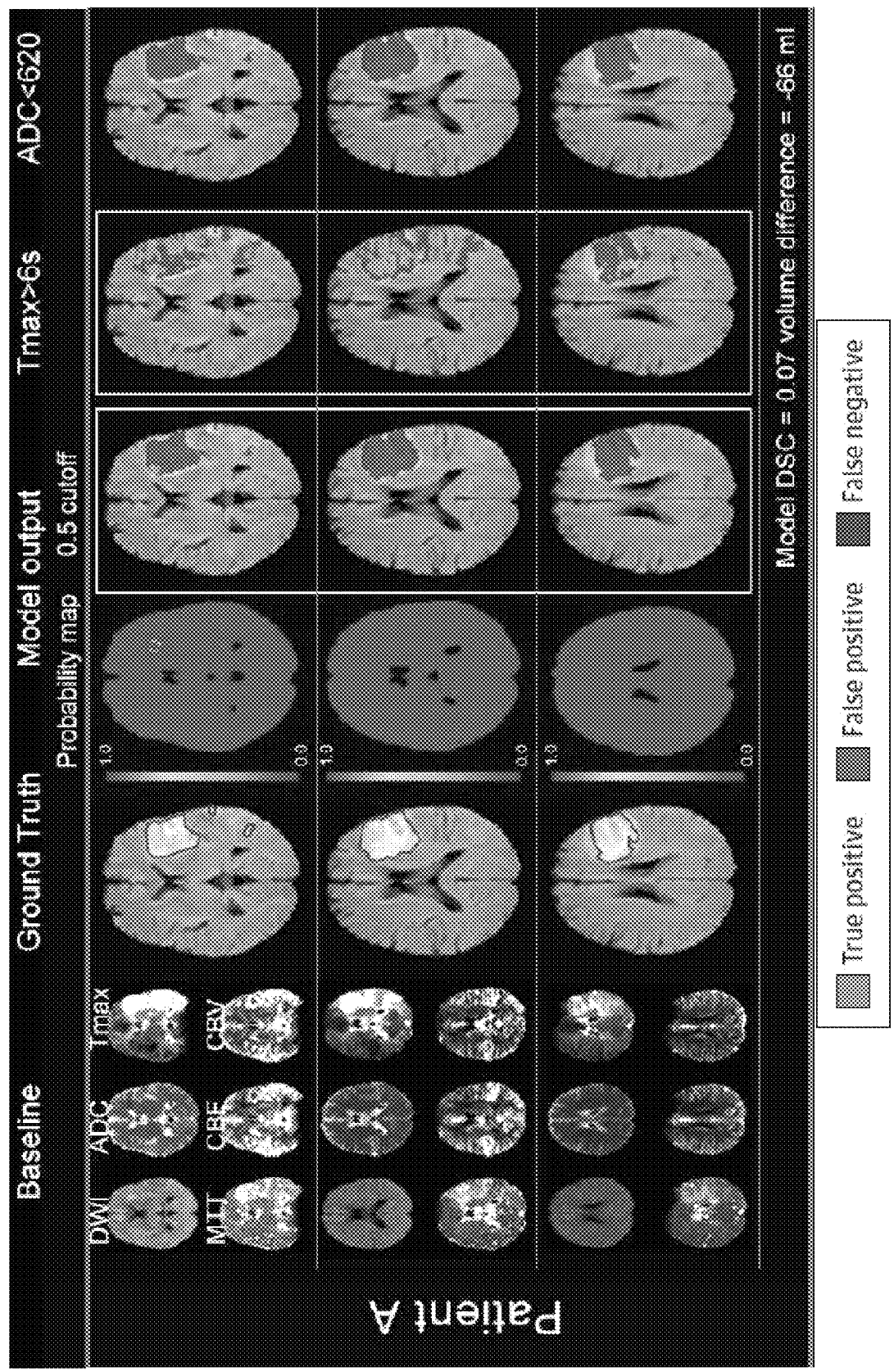
Figure 10B:
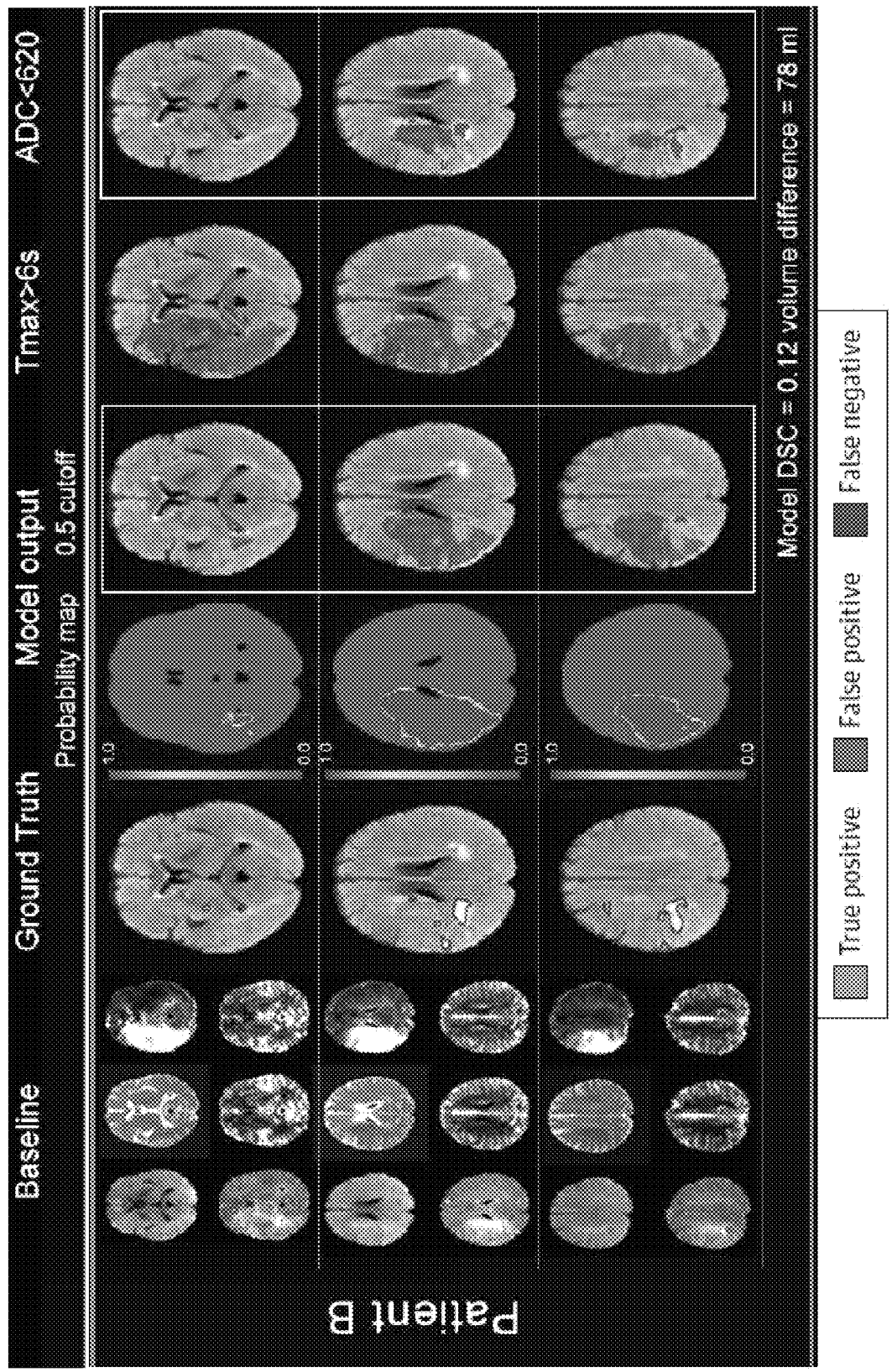
Figure 10C:
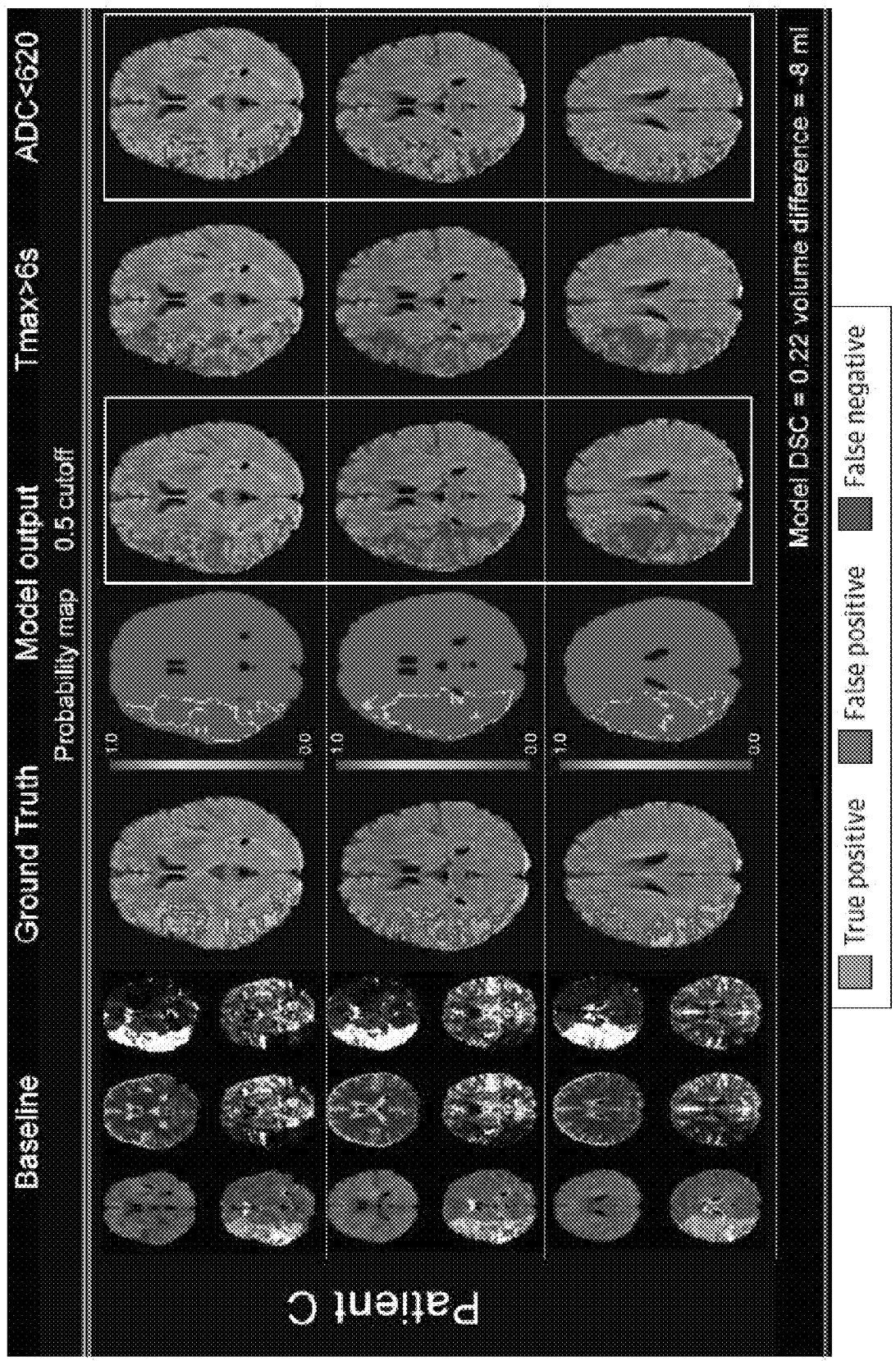

Model Performance in all Patients: The deep learning model had a median AUC of 0.92 (IQR 0.87, 0.96). Using a threshold of 0.5, the model had a median DSC overlap of 0.53 (IQR 0.31, 0.68), sensitivity of 0.66 (IQR 0.38, 0.86), specificity of 0.97 (IQR 0.94, 0.99), PPV of 0.53 (IQR 0.28, 0.74), volume error of 9 ml (IQR −14, 29 ml), and absolute volume error of 24 ml (IQR 11, 50 ml). The volume predicted from the model had excellent correlation with true lesion volume ($\rho_c$=0.74, 95% CI 0.66, 0.80) (FIG. 7). The lesion volume prediction of the model across all subgroups was more consistently stable than for the clinical thresholding models (ADC or ADC/Tmax union, FIG. 8). Representative cases are shown in FIGS. 9A, 9B and 9C for typical cases and FIGS. 10A, 10B, and 10C for atypical cases.

Model Performance in Minimal and Major Reperfusion Patients: Performance metrics in the minimal and major reperfusion patients with comparison to thresholding methods can be found in Table 2 (FIG. 11).

Figure 12A:
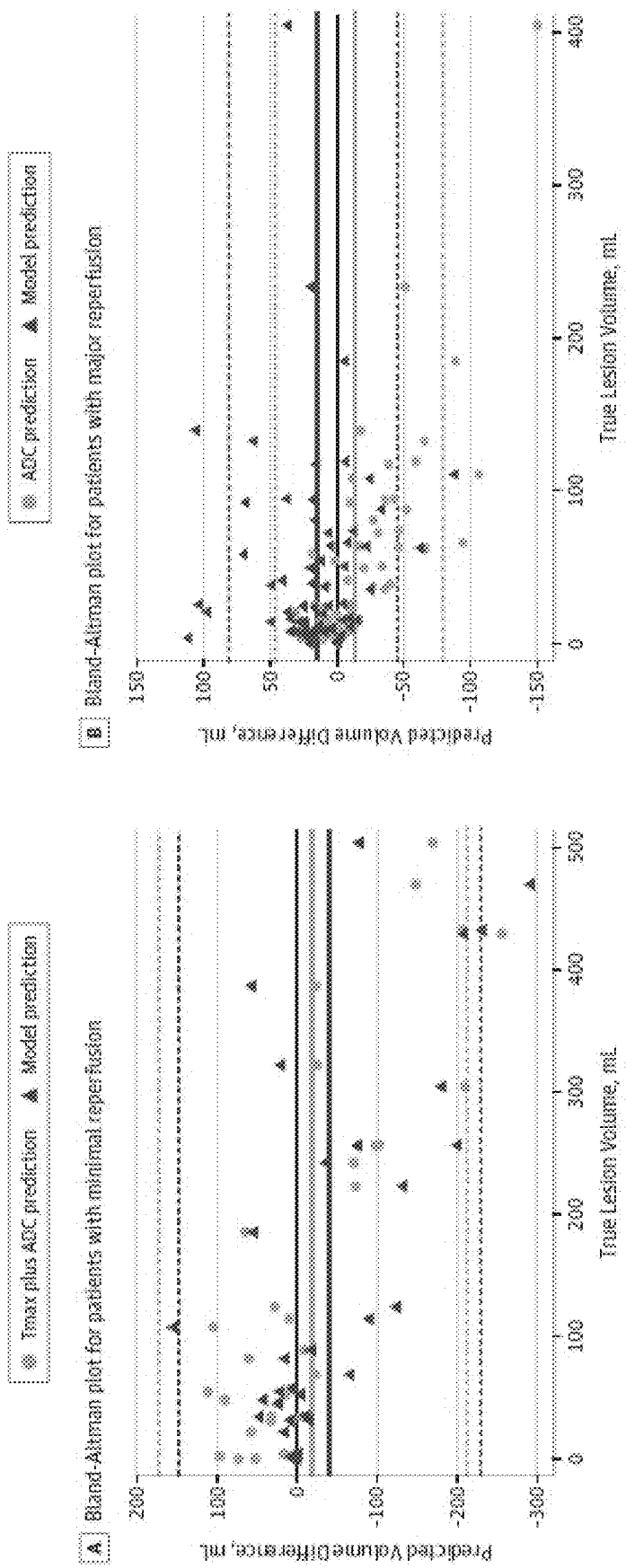
FIGS. 12A and 12B each provide data graphs of predictive model results compared with Tmax and ADC methods, generated in accordance with an embodiment of the invention.
Figure 12B:
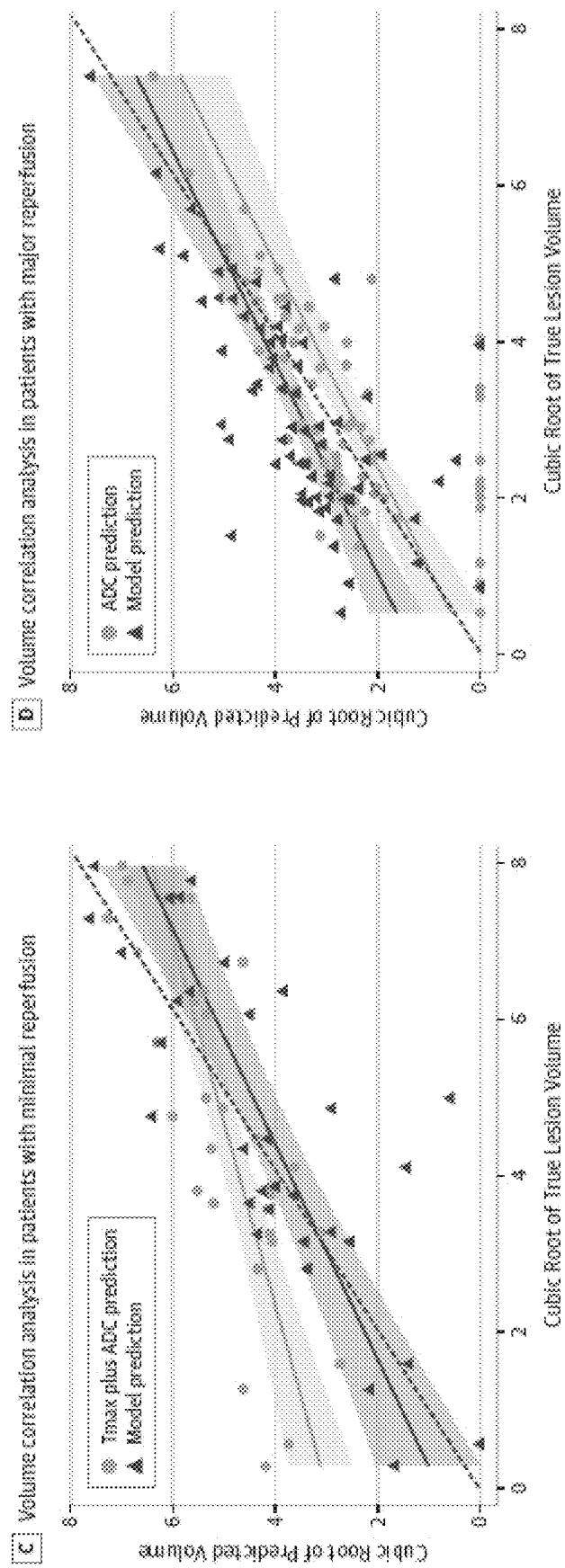

In minimal reperfusion patients, neither the proposed model nor the Tmax+ADC segmentation showed a difference between predicted and true lesion volume (p=0.07 and p=0.90, respectively). Volume prediction from Tmax+ADC ($\rho_c$=0.65, 95% CI 0.47, 0.77) and model ($\rho_c$=0.76, 95% CI 0.58, 0.87) yielded moderate and excellent agreement with true lesion volume, respectively. When compared with Tmax+ADC segmentation, the proposed model had higher PPV and specificity. In 17 patients with ground truth lesion volume <100 ml, the proposed model had a median volume error of 6 ml (IQR −5, 16), whereas Tmax+ADC segmentation overestimated the lesion volume by 32 ml (IQR 8, 61). In 15 patients with lesions >100 ml, both proposed model and Tmax+ADC segmentation underestimated the lesion volume (−90 ml [IQR −200, 21] and −73 ml [IQR −169, 10]), respectively (FIGS. 12A and 12B).

In major reperfusion patients, the proposed model overestimated lesion volume (p<0.001) while the ADC method underestimated volume (p<0.001). Volume prediction from ADC ($\rho_c$=0.63, 95% CI 0.47, 0.74) and model ($\rho_c$=0.67, 95% CI 0.52, 0.78) were similar. When compared with ADC thresholding, the proposed model had higher DSC and sensitivity but lower specificity. In 57 patients with ground truth lesions <100 ml, the proposed model overestimated the lesion size by 16 ml (IQR 0, 25) compared to that of ADC prediction of −2 ml (IQR −17, 7); in 9 patients with lesions >100 ml, the model overestimated the lesion by 16 ml (IQR −6, 37), whereas ADC underestimated by −59 ml (IQR −89, −39) (FIG. 3).

Model Performance in Partial and Unknown Reperfusion Patients: In partial and unknown reperfusion patients, the model had moderate to excellent agreement between predicted and true lesion volume ($\rho_{pc}$=0.69, 95% CI 0.51, 0.82, and $\rho_c$=0.75, 95% CI 0.58, 0.86, respectively). Volumetrically, the proposed model did not show a significant difference from the true lesion (volume error of 9 ml [IQR −31, 37] and 6 ml [IQR −11, 32], respectively).

Discussion

This example demonstrates that an attention-gated U-net deep learning model trained using only baseline multi-sequence MRI data could be used to predict 3-7 day infarct lesions. The model was trained without including information about reperfusion status, yet it had comparable performance in patients with and without major reperfusion compared with a common clinically-used ADC and Tmax thresholding software package. Furthermore, it performed similarly well in patients with partial or unknown reperfusion status where neither of the traditional prediction methods based on the diffusion-perfusion mismatch paradigm apply.

In minimal reperfusion patients, the proposed model outperformed the clinical thresholding method for PPV and specificity while maintaining comparable DSC and sensitivity. For lesions <100 ml, where small differences are clinically most relevant, the proposed model predicted volume more accurately than the clinical thresholding method. For those patients with major reperfusion, the proposed model outperformed the clinical thresholding method for DSC and sensitivity. In these patients, the model tended to overestimate the final infarct lesion while the ADC segmentation tended to underestimate the lesion. The clinical ADC thresholding method outperformed the proposed model for specificity, which is expected, as the area of infarct at baseline rarely shows reversibility. For example, only one patient in the cohort demonstrated any ADC reversal (FIG. 10B), which can occur immediately after reperfusion, but which does not generally persist. The performance of the proposed model is significantly better than that reported in the previous literature, with almost twice the overlap of the predicted and true lesions of these earlier methods.

Although imaging features at baseline may be associated with successful therapy, the effect of treatment and subsequent infarct growth is difficult to predict. The prediction of the proposed model may act as a "most likely" final infarct for patients upon arrival, given the most common treatment decisions and their success rate, which can provide additional information other than mismatch profile for the decision-making. Since the proposed model predicts the infarct lesion at 3-7 days when the size of the lesion is largest due to acute vasogenic edema, it would be helpful to guide treatment decisions and coordinate clinical resources such as early preparation for decompression surgery and osmotherapy. Patient selection for future clinical trials of neuroprotective agents based on imaging also becomes relevant. The proposed model, providing a comprehensive estimation of the subacute stroke lesion that includes area of edema and hemorrhagic transformation, could serve as a marker for the patient selection in such trials. Further studies are warranted to explore the association between model prediction and outcomes such as cerebral herniation and functional outcome.

Example 2

Predicting PET Cerebrovascular Reserve with Deep Learning Using Baseline MRI: a Pilot Investigation of a "Drug-free" Brain Stress Test Many patients with chronic cerebrovascular disorder (CVD) are at increased risk of ischemic stroke because they have poor cerebrovascular reserve (CVR), defined as the ability to increase cerebral blood flow (CBF) in response to a vasodilatory stimulus. Clinically, CVR is commonly measured using paired CBF measurements before and after a vasodilator drug, typically acetazolamide (ACZ).

ACZ is generally safe but contraindicated in patients with sulfa allergies or severe kidney and liver disorder. Furthermore, patients may present with stroke-like symptoms during the test. These symptoms, although transient and rare, unsettle patients and medical staff. Reported reactions include common mild adverse reactions, such as headache, flushing, and malaise and rare severe adverse events, including pulmonary edema, Stevens-Johnson syndrome, and anaphylaxis. Finally, avoiding an intravenous medication makes the test easier to administer. Assessing CVR without ACZ injection is thus valuable for the clinical evaluation of patients with cerebrovascular disorder.

Several studies have shown that CVR in patients with CVD may be predicted from baseline perfusion or structural images, including mean transit time and Tmax from dynamic perfusion CT and MRI, arterial transit time (ATT) from arterial spin labeling (ASL), and the "ivy sign" on T2-FLAIR images. Most of these studies used a linear model with single input to make predictions. However, multiple other factors may also affect CVR, including the severity of arterial stenosis, baseline CBF, old strokes, and brain location. Deep learning, which recently has shown remarkable performance in the reconstruction and generation of brain images, provides a potential method to construct a multivariate, non-linear model to improve prediction of CVR.

Moyamoya disorder is a progressive occlusive arteriopathy of the anterior circulation that occurs primarily in young patients without other co-morbidities. As such, these patients are ideal study participants to investigate severely altered cerebral hemodynamics. In this study, we obtained simultaneous [$^{15}$O]-water PET/MRI in patients with Moyamoya disorder and healthy controls, including PET and ASL MRI scans of brain perfusion. It was hypothesized that deep learning models can predict voxelwise CVR from baseline (i.e., pre-ACZ) structural and perfusion images, using PET-CVR as the ground truth. Once validated, such an approach would allow CVR estimation in settings where pharmacological vasodilation is contraindicated or undesirable.

Materials and Methods

Participants: This HIPAA compliant retrospective study was approved by our Institutional Review Board. Written informed consent was obtained from all participants. From April 2017 through May 2019, consecutive patients with Moyamoya disorder were recruited through the Neuroscience Clinics and age-matched healthy controls. Inclusion criteria included age of 15 years or older and ability to comply with all studies. Exclusion criteria was poor CVR response to ACZ (defined as an absolute PET-CBF change in cerebellum of less than 10 ml/100 g/min).

PET/MRI Acquisition: Images were acquired on a simultaneous time-of-flight 3.0 T PET/MRI scanner (SIGNA, GE Healthcare, Waukesha, WI). Each participant received two simultaneous PET/MRI perfusion scans, at baseline and 15 min after intravenous administration of acetazolamide (15 mg/kg with a maximum of 1 g).

Static PET images were reconstructed from 2 min of detected counts after injection. The reconstruction used time-of-flight ordered subset expectation maximization and included corrections for decay, scatter, random counts, dead time, and point-spread function compensation. MRI attenuation correction was performed with the vendor's atlas-based method.

Each MRI perfusion scan included two pseudocontinuous ASL scans and a phase-contrast MRI scan. Standard single-delay ASL with consensus parameters and a Hadamard-encoded multidelay ASL sequence were obtained. Phase-contrast MRI was acquired to measure total brain blood flow at one slice in the cervical region perpendicular to the internal carotid and vertebral arteries. T1-weighted (T1W) 3D high-resolution images and T2-weighted fluid-attenuated inversion recovery (T2-FLAIR) images were acquired for all participants. Detailed MRI parameters are listed in Table 3 (FIGS. 13A and 13B).

CBF quantification: Quantitative PET-CBF maps were generated by combining phase-contrast MRI and [$^{15}$O]-water PET using the PC-PET method, which takes the spatial distribution information from the PET maps, and scales it to whole-brain mean CBF measured by simultaneous phase-contrast MRI. Quantitative ASL-CBF maps were generated from the ASL difference images with proton density-weighted reference images. For single-delay ASL, CBF maps were quantified using the single-compartment model. For multidelay ASL, arterial transit time (ATT) maps were measured using the signal-weighted delay approach and ATT-corrected CBF maps were generated from the two-compartment model.

Image Processing: All images were coregistered to T1W structural images using Statistical Parametric Mapping software (SPM12, Wellcome Centre, London, UK), and then normalized to the Montreal Neurological Institute (MNI) template by using Advanced Normalization Tools (ANTs, stnava.github.io/ANTs) (see N. J. Tustison, et al., Neuroimage. 2014; 99:166-179, the disclosure of which is incorporated herein by reference). Relative CBF change due to vasodilation (rΔCBF) was defined as the difference between post-ACZ CBF and pre-ACZ CBF, normalized to each subject's mean CBF change within the cerebellum, based on a spatially unbiased atlas template of human cerebellum (SUIT), to account for individual differences in global CBF augmentation. All rΔCBF maps were smoothed by a 10-mm Gaussian filter. rΔCBF maps measured by PET (PET-rΔCBF) and multidelay-ASL (ASL-rΔCBF) were calculated.

Figure 14:
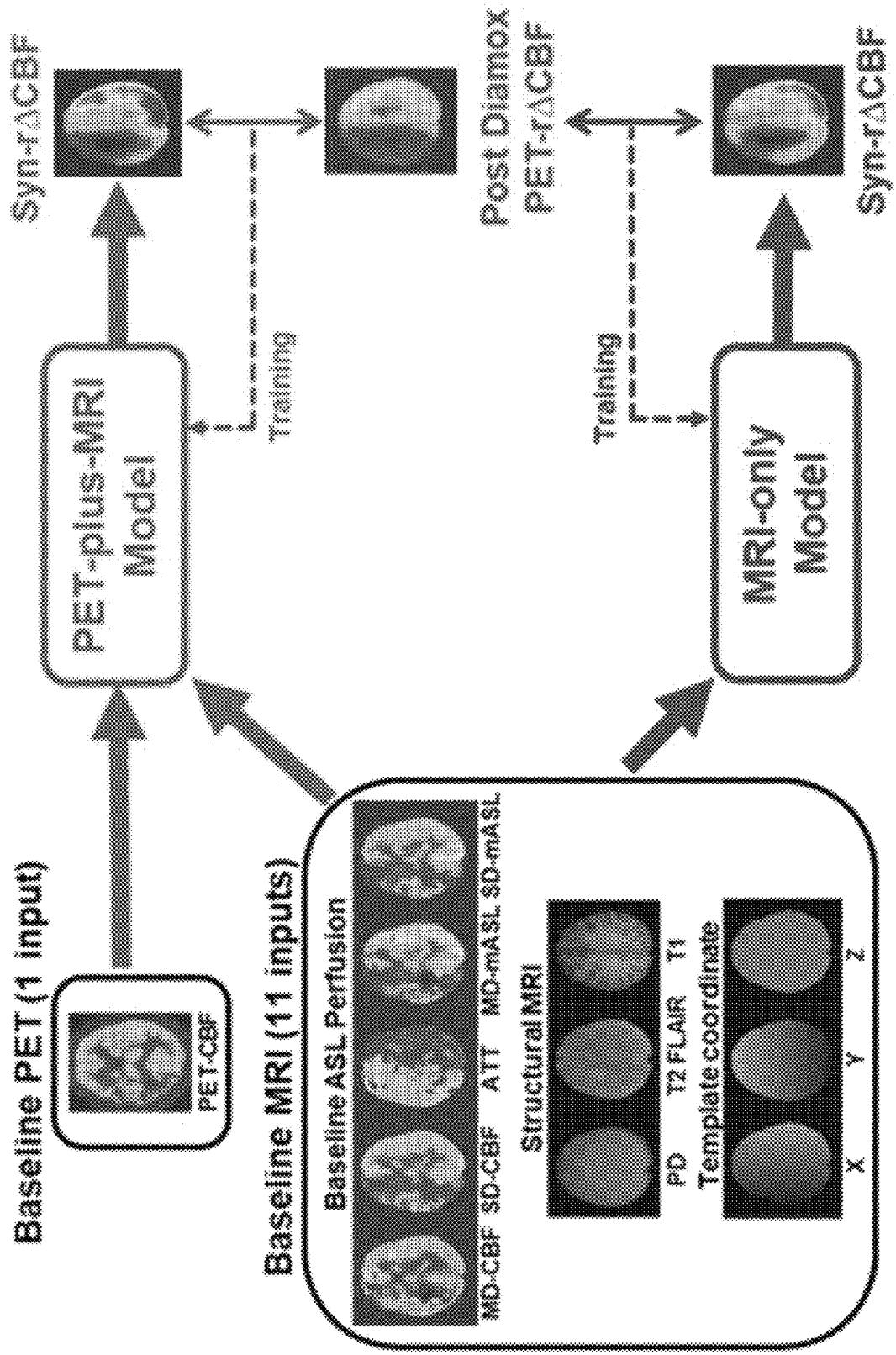
FIG. 14 provides a flow diagram of a method to train a convolutional neural network to predict cerebrovascular reserve in accordance with an embodiment of the invention.
Figure 15:
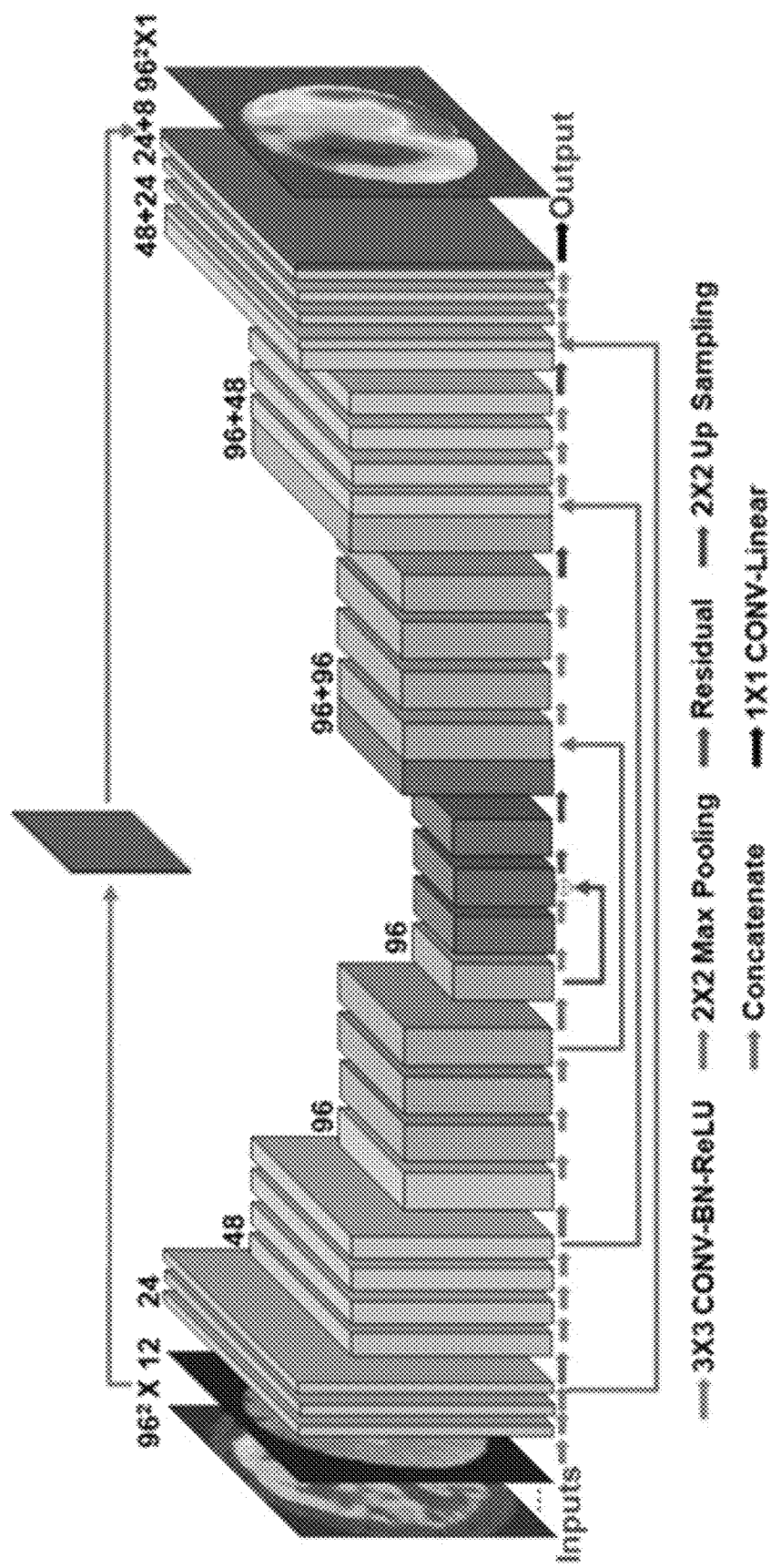
FIG. 15 provide a schema of the architecture of a convolutional neural network to predict cerebrovascular reserve in accordance with an embodiment of the invention.

Deep Learning Model Implementation: Two deep learning models were constructed to predict ground truth PET-rΔCBF (FIG. 14). The first model (PET-plus-MRI model) included 12 inputs from both baseline PET and MRI, including 1) baseline PET-CBF; 2) baseline ASL: CBF and mean ASL difference signal from single-delay and multidelay ASL, proton density-weighted images from single-delay ASL and ATT from multidelay ASL; 3) structural scans: T1W and T2-FLAIR images, which provide information of tissue composition and presence of old strokes; and 4) the voxel coordinate in MNI template space, which provides information on brain location. In the second model (MRI-only model), we excluded the baseline PET-CBF map from the inputs. The model architecture was a 2D encoder-decoder with a U-net structure, shown in FIG. 15. In brief, each encoder layer consists of three convolutional layers with 3×3 kernels, batch normalization, rectified linear unit (ReLU) activation layer, and 2×2 max-pooling. A residual connection is placed at the central layer. In the decoder portion, the data in the encoder layers are concatenated to retain high-resolution information. Finally, linear interpolation is performed to give the output of synthetic rΔCBF (syn-rΔCBF) maps.

Deep Learning Model Training and Testing: All input images except ATT were normalized to the corresponding whole brain mean. ATT was normalized by 3.7 sec, which was the longest post-label delay used. Input images were augmented by flipping along x and y directions. The cost function was defined as weighted mean absolute error (WMAE) minus 0.1 times structural similarity index metric (SSIM): WMAE was weighted by 3-fold in voxels with PET-rΔCBF<1, to emphasize accuracy in low CVR regions. SSIM was added as a perceptual loss, which improves performance for image generation. Adaptive moment estimation (ADAM) was used as the optimization method. The initial learning rate was 0.0006 with a batch size of 160 slices and 40 epochs.

Six-fold cross-validation was used. The 36 PET/MRI datasets were divided into 6 sub-groups, each consisting of 6 datasets from 4 patients with Moyamoya disorder and 2 healthy controls. For each fold, the datasets from 5 of the sub-groups (30 datasets total) were used for training, from which 10% of the images were randomly selected for validation. This trained network was then tested on the unused sub-group (6 datasets total). All training and testing were performed using a Tesla V100 PCIe GPU (Nvidia, Santa Clara, CA).

Assessment of Image Quality: Syn-rΔCBF and ASL-rΔCBF image quality were quantitatively evaluated by root mean square error (RMSE), peak signal-to-noise ratio (PSNR) and SSIM, compared with the ground truth PET-rΔCBF maps. All three metrics were calculated within the MNI-based brain mask for each slice and averaged for each participant.

Assessment of rΔCBF Quantification: rΔCBF was measured in 90 supratentorial cortical regions of interest based on the AAL2 template in each participant. Mixed effect models adjusted for within-subjects clustering, by assuming within-subject errors and random effects are "normally distributed", and Bland-Altman plots examined correlation and agreement between syn-rΔCBF, ASL-rΔCBF maps, and the ground truth PET-rΔCBF maps.

Figure 16:
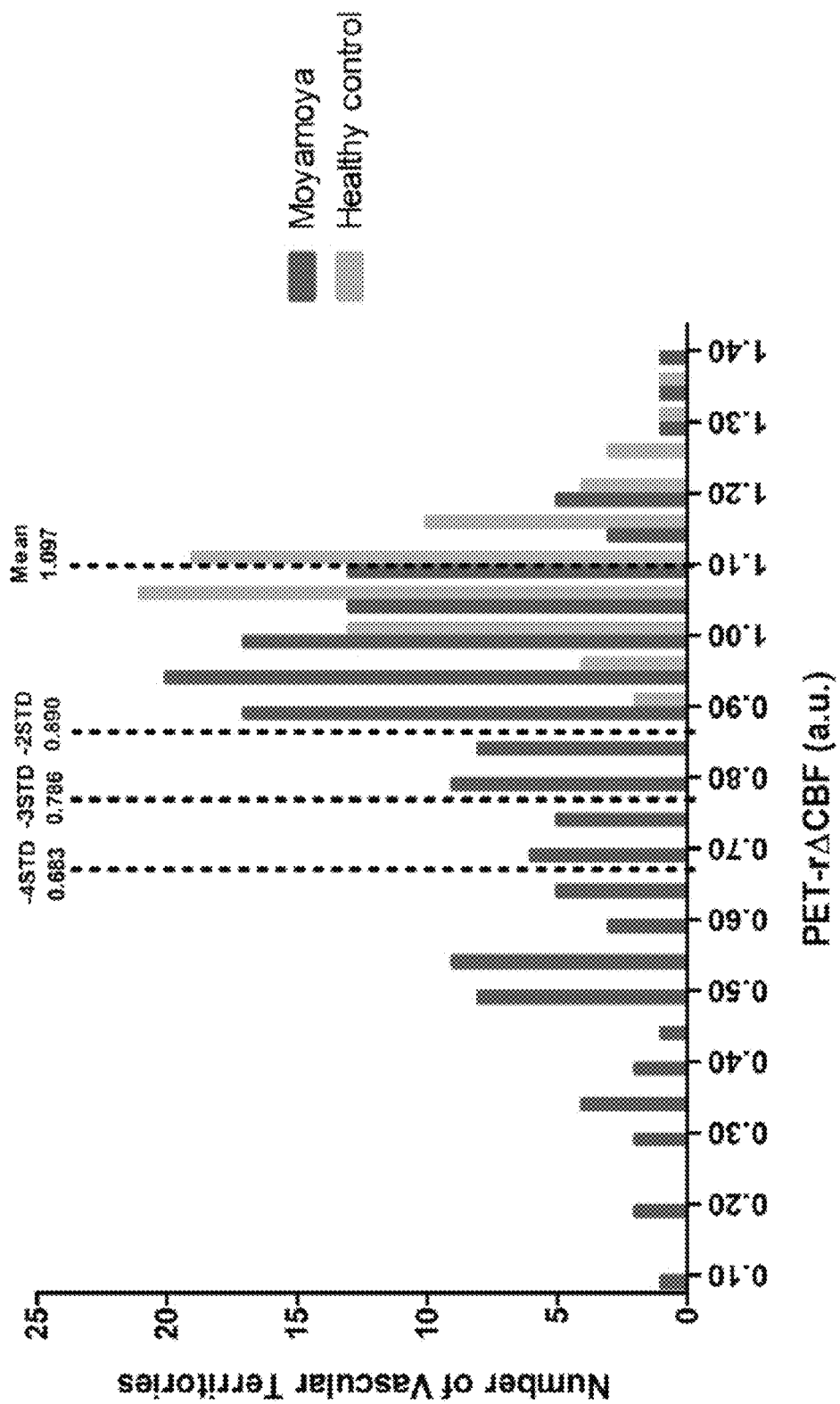
FIG. 16 provides cerebrovascular reserve results of Moyamoya patients and healthy controls, utilized in accordance with an embodiment of the invention.

Detection of Impaired CVR: For each patient with Moyamoya disorder, rΔCBF was calculated in 6 vascular territories (anterior, middle, and posterior, in each hemisphere), corresponding to 2 slice locations of the Alberta Stroke Programme Early Computed Tomography Score (ASPECTS) (see P. A. Barber, Lancet. 2000; 355(9216): 1670-1674, the disclosure of which in incorporated herein by reference). Threshold values of impaired PET-rΔCBF were defined as 3STD below the mean PET-rΔCBF values in the healthy controls (FIG. 16). The area under the receiver-operator characteristic (ROC) curve (AUC) was used to evaluate the diagnostic performance of syn-rΔCBF and ASL-rΔCBF at identifying territories with impaired CVR. A total of 144 vascular territories from the 24 patients were included in the analysis. Sensitivity and specificity for each method were calculated at the model threshold that maximized the Youden index. To explore the diagnostic performance in a wider range, thresholds of 2STD and 4STD below the healthy control mean were also evaluated.

Statistical Analyses: The Friedman test was used to compare image quality between the PET-plus-MRI model, MRI-only model, and ASL methods. Post-hoc comparison was performed using Dunn's multiple comparison test. The differences of correlation coefficient and AUC between each methods were compared using Wilcox-Muska test and DeLong's test, respectively. The mixed effect model analyses, Wilcox-Muska test and DeLong's test were performed with Stata version 15.1 (StataCorp LP, College Station, TX)

and the other analyses were performed with GraphPad Prism version 5 (GraphPad Software, La Jolla, CA).

Results

Participant Characteristics: From the 25 patients with Moyamoya disorder who completed all studies, one patient failed to response to ACZ and was excluded. Twenty-four patients (mean age±STD, 41±12 years; 17 women) and 12 age-matched healthy controls (39±16 years; 9 women) were included. Participant demographics are summarized in Table 4 (FIGS. 17A and 17B).

Figure 18:
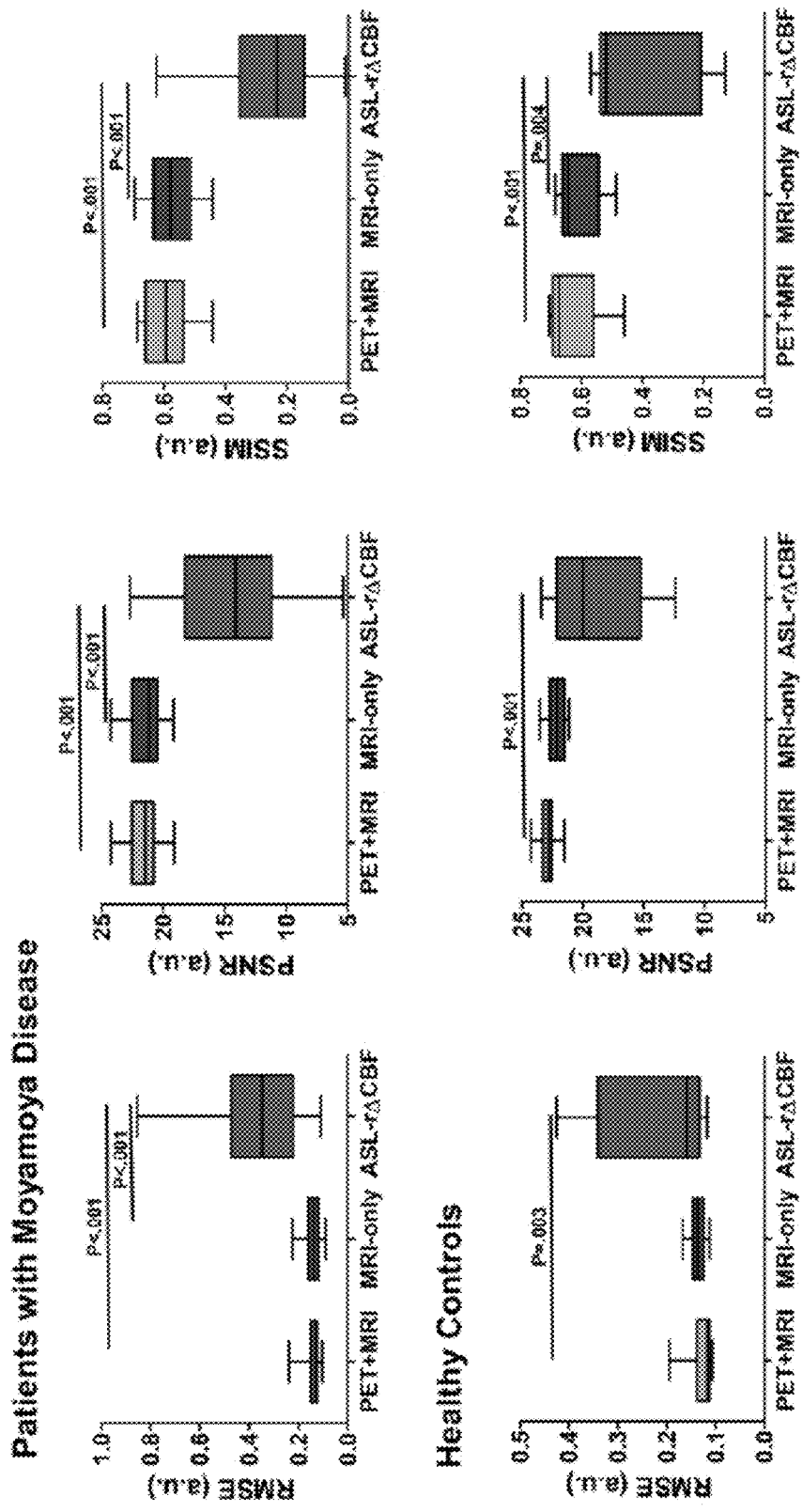
FIG. 18 provides data graphs of predictive model results compared with ASL methods, generated in accordance with an embodiment of the invention.

Image Quality Assessment: FIG. 18 shows the image quality metrics for each method. In patients with Moyamoya disorder, both deep learning models performed better than ASL-rΔCBF for all metrics (all p<0.001). In healthy controls, the PET-plus-MRI model outperformed ASL-rΔCBF for all metrics (p=0.003 for RMSE, p<0.001 for PSNR and SSIM), while the MRI-only model was only better for SSIM (p=0.004). No differences in image quality were observed between the two models when comparing patients and healthy controls (RMSE, PSNR, SSIM: p=0.39, 0.39, 0.25 for patients, p=0.31, 0.10, 0.10 for controls). The details of image quality metrics are listed in Table 5 (FIGS. 19A and 19B.

Figure 20A:
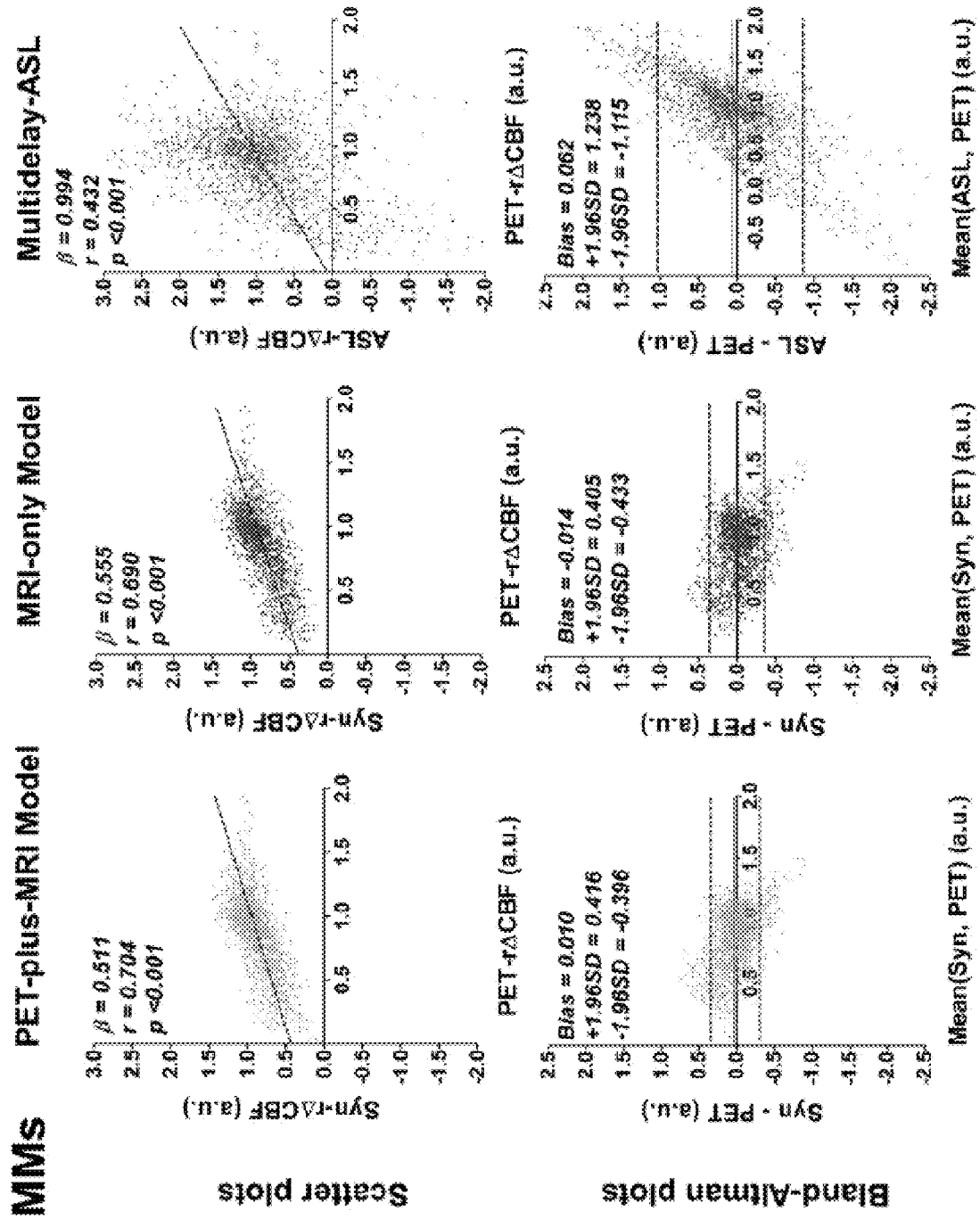
FIGS. 20A and 20B each provide data graphs of predictive model results compared with ASL methods, generated in accordance with an embodiment of the invention.
Figure 20B:
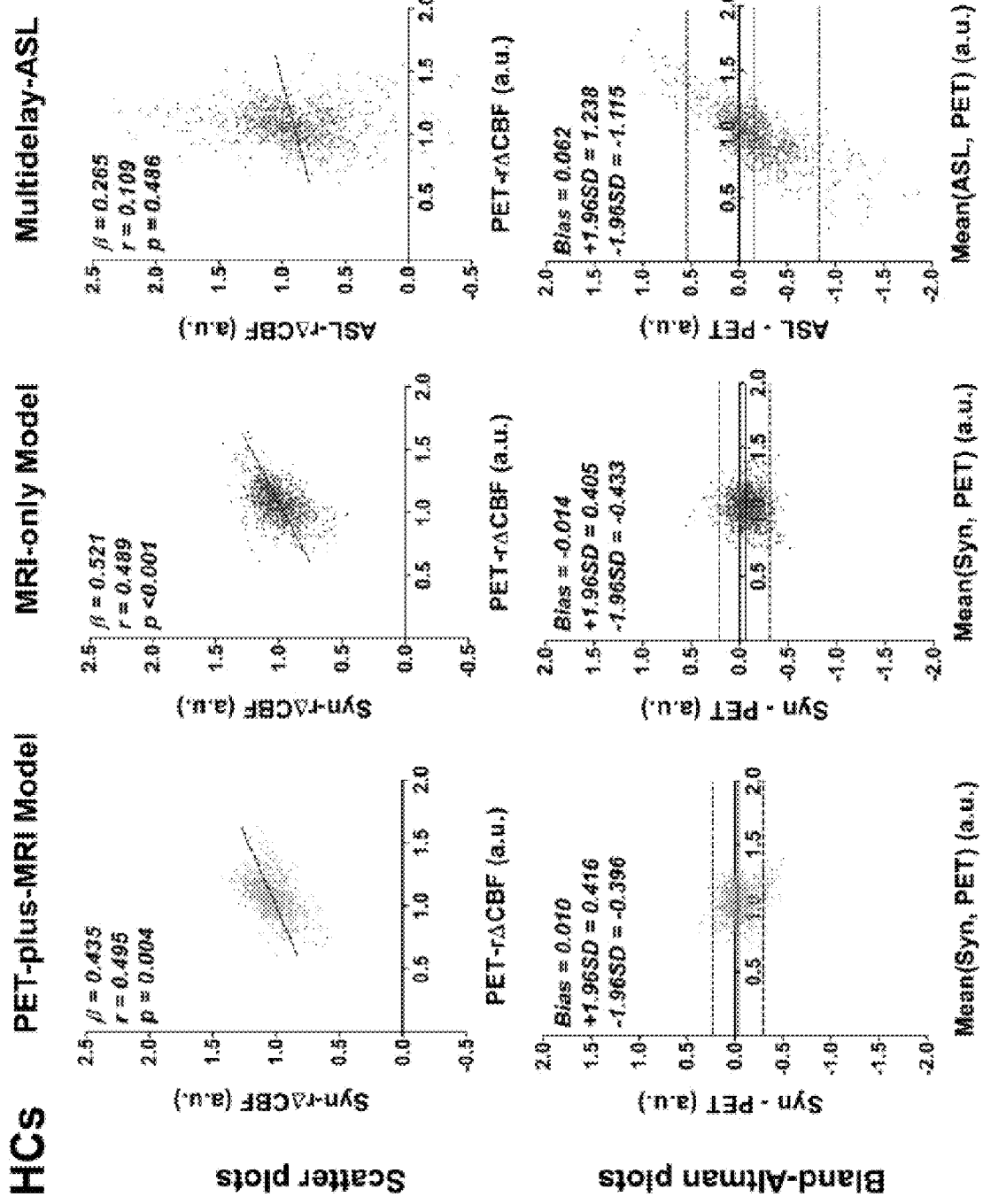

CVR Quantification Assessment: In patients with Moyamoya disorder, rΔCBF from both deep learning models and ASL-rΔCBF were all correlated with PET-rΔCBF (FIG. 20A), though the deep learning models had better correlation than ASL-rΔCBF (both p<0.001). In healthy controls, rΔCBF values from both models also correlated with PET-rΔCBF (p<0.001 [PET-plus-MRI] and =0.004 [MRI-only]), while ASL-rΔCBF did not correlate with PET-rΔCBF (p=0.49) (FIG. 20B). In both groups, the correlation coefficients were not different between the two models (p=0.62 [patients] and 0.95 [controls]). On Bland-Altman plots, rΔCBF values from both models showed less bias and lower variance than ASL-rΔCBF for both groups. Moreover, proportional bias existed for ASL-rΔCBF in both groups, showing overestimation at higher rΔCBF and underestimation at lower rΔCBF (FIG. 20B).

Figure 21:
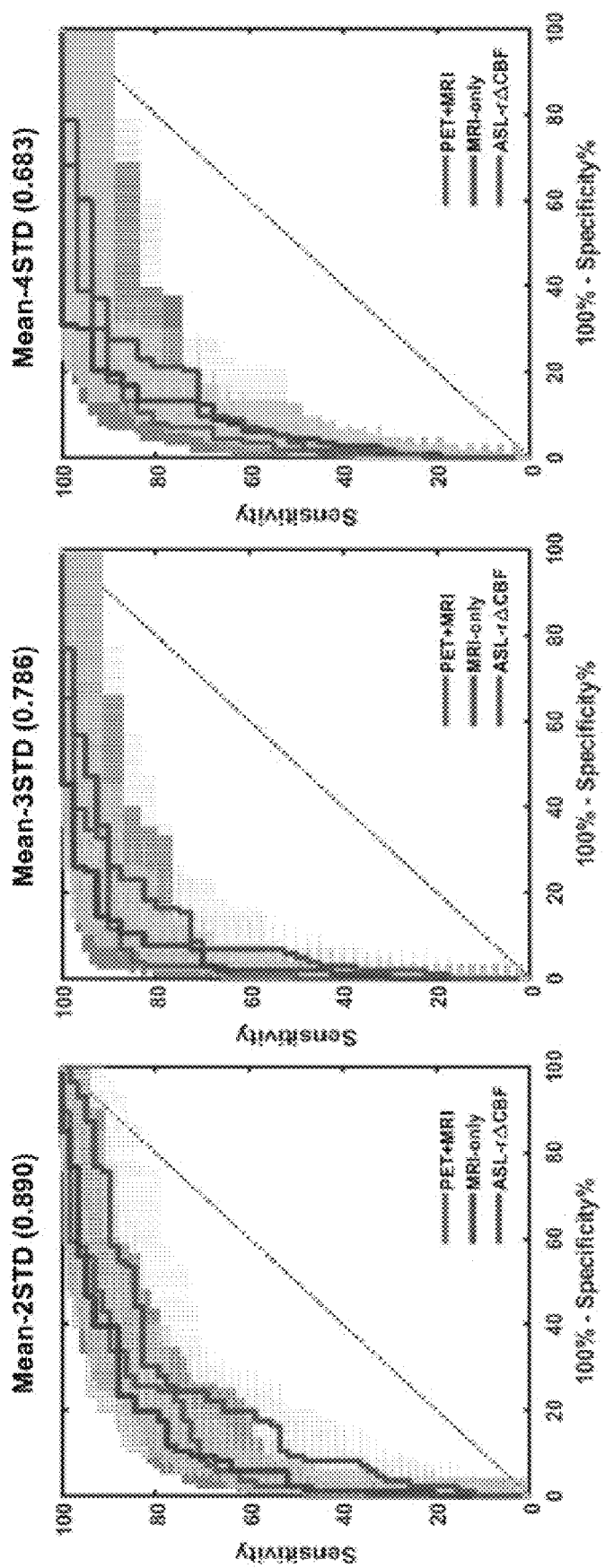
FIG. 21 provide AUC graphs of predictive models compared with ASL methods, generated in accordance with an embodiment of the invention.

Detection of Impaired CVR: FIG. 21 shows the ROC curves and Table 2 (FIG. 22) shows the AUC, sensitivity, and specificity of both deep learning models and ASL-rΔCBF to identify vascular territories with impaired PET-rΔCBF in patients with Moyamoya disorder. For each threshold of impaired PET-rΔCBF, the AUC of both models were higher than that of ASL-rΔCBF. The AUCs for PET-plus-MRI model, MRI-only model, and ASL-rΔCBF were 0.95 (95% confidence interval [CI]: 0.90, 0.99), 0.95 (95% CI: 0.91, 0.98) and 0.89 (95% CI: 0.83, 0.95) for a threshold of 3STD below mean in healthy controls. A similar pattern was seen for milder or more severe CVR thresholds. The deep learning models consistently outperformed ASL-rΔCBF, even though the ASL images were acquired pre- and post-ACZ while the deep learning models predicted CVR using pre-ACZ images only (FIG. 22). At the 3STD threshold, sensitivity/specificity for PET-plus-MRI model, MRI-only model, and ASL-rΔCBF were 35 of 40 (88%)/97 of 104 (93%), 35 of 40 (88%)/93 of 104 (89%), and 33 of 40 (83%)/85 of 104 (82%), respectively.

Figure 23:
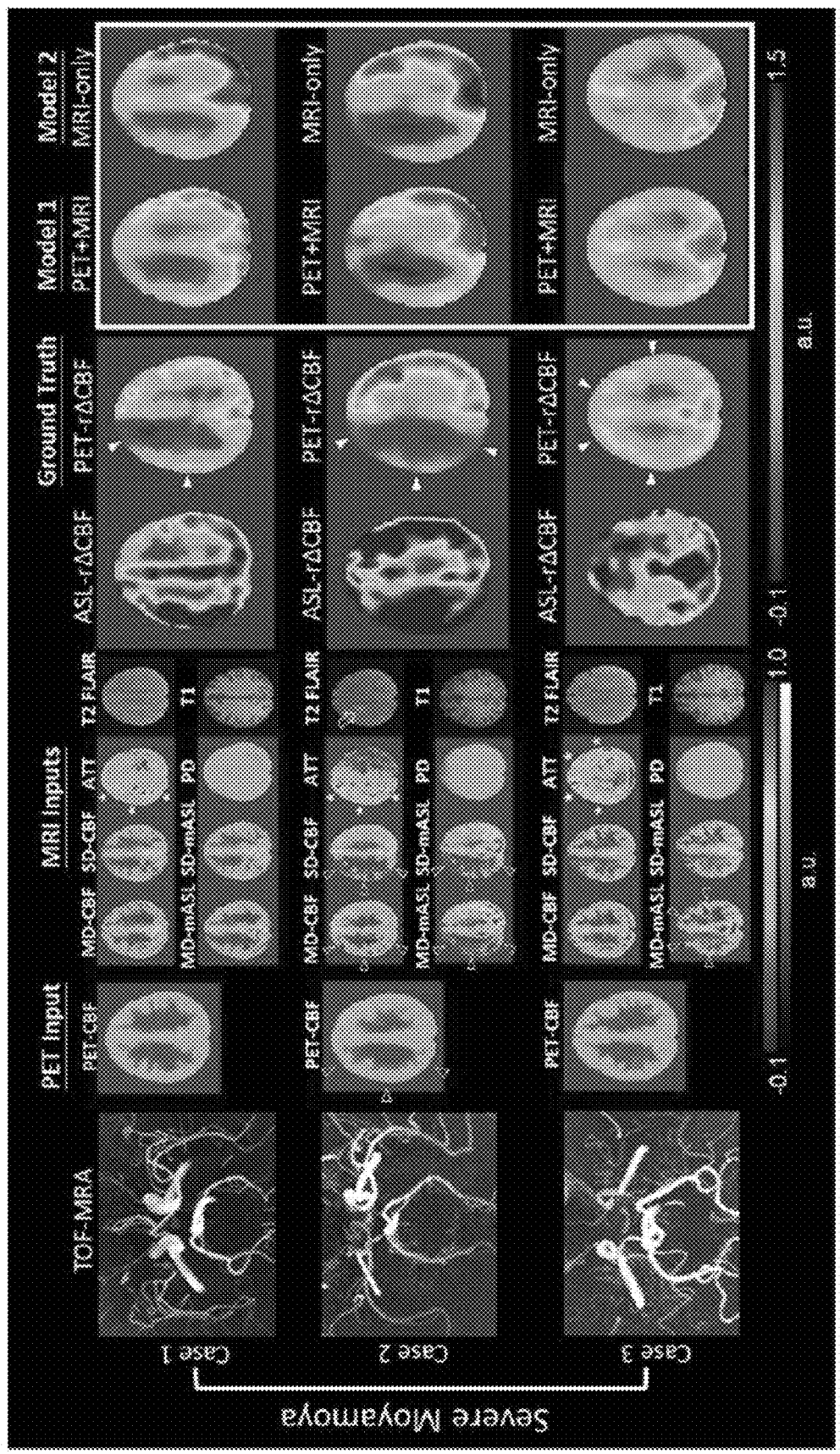
FIGS. 23 and 24 each provide predicted images and actual images of Moyamoya and healthy patients, generated in accordance with an embodiment of the invention.
Figure 24:
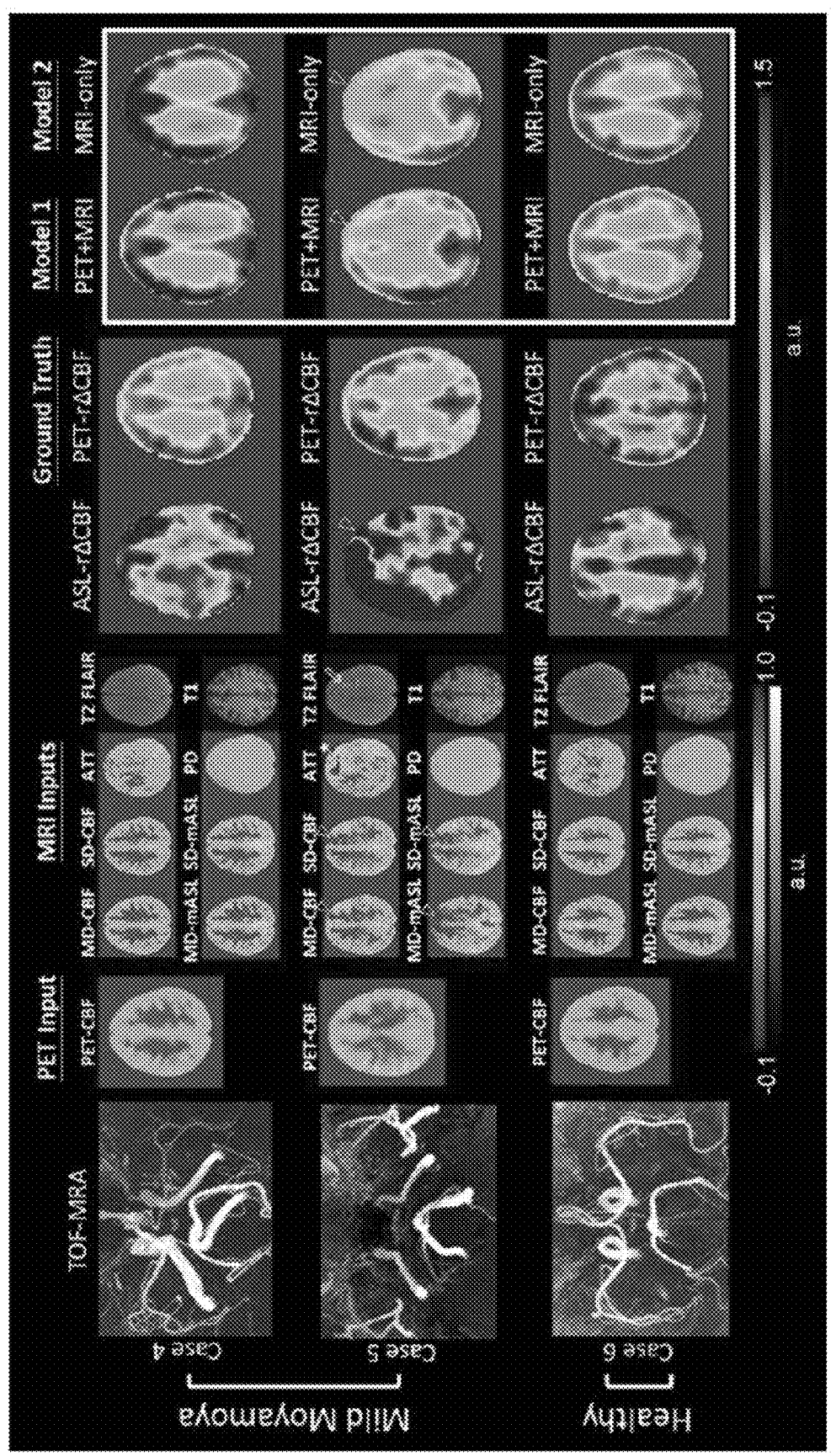

Image Assessment: Images from three patients with severe Moyamoya disorder, defined as having impaired PET-rΔCBF in any vascular territory, are shown in FIG. 23. Syn-rΔCBF of both models visually show higher image quality than ASL-rΔCBF and are similar to PET-rΔCBF. Generally, brain regions with lower CBF, longer ATT, and chronic infarcts on baseline images had lower rΔCBF. ASL tended to underestimate rΔCBF in regions with low PET-rΔCBF, consistent with the proportional bias on Bland-Altman plots. FIG. 24 presents two patients with mild Moyamoya disorder without impaired CVR and a healthy control. In mild cases, baseline CBF was usually preserved and ATT was not severely prolonged.

Discussion

Deep learning models were constructed that combined multi-contrast information from baseline PET and MRI to predict cerebrovascular reserve, using simultaneously acquired [$^{15}$O]-water PET maps as the reference. Both models, whether using only pre-acetazolamide MRI or MRI and PET, had better image quality (all p<0.001 in patients) and quantification accuracy than arterial spin labeling (ASL)-derived maps (correlation coefficient=0.704 [PET-plus-MRI], 0.690 [MRI-only] versus 0.432 [ASL], both p<0.001, in patients). Both models also demonstrated higher or comparable diagnostic performance than ASL to identify impaired cerebrovascular reserve. Furthermore, the MRI-only model performed similarly to the PET-plus-MRI model in image quality, quantification accuracy, and diagnostic performance (all p>0.05 in the comparison between the two models).

Baseline perfusion parameters can predict CVR. Among common perfusion parameters, timing parameters from dynamic susceptibility contrast methods, such as mean transit time and Tmax, best reflect CVR in Moyamoya disorder and atherosclerotic steno-occlusive disorder. ATT derived from multidelay ASL also correlates with CVR and could predict CVR impairment in unilateral steno-occlusive disorder. Baseline CBF is another important factor to determine CVR. In patients with CVD, when cerebral perfusion pressure begins to decrease, autoregulation causes vasodilation to maintain CBF. Further perfusion pressure decreases cause decreased CBF, leading to a non-linear relationship with CVR. Patients with decreased baseline CBF are likely to have worse CVR than patients with normal baseline CBF. Given that CVR changes are expected to be non-linear functions of perfusion parameters, a non-linear, data-driven method such as deep learning is expected to provide more accurate predictions than these linear predictors.

Structural imaging could also contribute valuable information to predict CVR. The presence of leptomeningeal collaterals, such as the "ivy sign" on T2-FLAIR and ASL arterial transit artifact are associated with reduced CVR in chronic CVD. White matter hyperintensities have lower CVR than normal appearing white matter and chronic infarcts generally have poor CVR. Furthermore, CVR can have considerable variation among different brain regions and between white matter and gray matter. This information can be provided by anatomical images and template coordinates but is hard to integrate into traditional regression models. Deep learning constructs a multimodal, non-linear model, incorporating the inherently high-dimensional inputs of baseline perfusion, structure, and location, to predict voxelwise CVR.

The synthetic CVR maps had significantly higher image quality and quantification accuracy than ASL-rΔCBF even though the latter directly measured post-ACZ information. The deep learning models learned the CVR prediction from PET, which was less sensitive to transit delay and flow velocity changes and had higher SNR than ASL.

Both deep learning models showed high diagnostic performance in identifying vascular territories with impaired CVR. Yun et al. reported AUCs between 0.85 and 0.94 using CVR measured by single-delay ASL to identify impaired CVR regions measured by SPECT in patients with Moyamoya disorder (see T. J. Yun, *Radiology*. 2016; 278

(1):205-213, the disclosure of which is incorporated herein by reference). Furthermore, Choi et al. (H. J. Choi, et al., *Am J Neuroradiol*. 2018; 39(1):84-90, the disclosure of which is incorporated herein by reference) used baseline ATT from ASL to identify impaired CVR in unilateral steno-occlusive disorder, with an AUC of 0.89. Both our models showed comparable or higher AUCs at all tested thresholds.

DOCTRINE OF EQUIVALENTS

While the above description contains many specific embodiments of the invention, these should not be construed as limitations on the scope of the invention, but rather as an example of one embodiment thereof. Accordingly, the scope of the invention should be determined not by the embodiments illustrated, but by the appended claims and their equivalents.

What is claimed is:

1. A method of assessing the ability of an experimental treatment to ameliorate the medical disorder, comprising:
   capturing or having captured a set of one or more baseline biomedical images from each subject of a cohort of subjects, wherein each subject of the cohort has a medical disorder that is shared among the subjects;
   for each subject of the cohort, utilizing or having utilized a trained and validated predictive model and the subject's set of baseline biomedical images to predict the progression of the subject's disorder without the experimental treatment, wherein the predicted disorder progression of each subject of the cohort is utilized as a surrogate for a control arm in a clinical experiment;
   for each subject of the cohort, and after having captured a set of one or more baseline biomedical images from each subject, administering or having administered the experimental treatment to the subject, wherein ability of the experimental treatment to ameliorate progression of the medical disorder is being assessed by the administration;
   for each subject of the cohort, capturing or having captured a set of one or more experimental biomedical images during or at the end of the experimental treatment; and
   for each subject of the cohort, assessing the ability of the experimental treatment to ameliorate progression of the medical disorder by comparing the data of the captured experimental biomedical images with the data of the predicted disorder progression;
   wherein the data of the captured experimental biomedical images represents the results of the experimental treatment and the data of the predicted disorder progression represents the control arm.

2. The method as in claim 1, wherein the trained and validated predictive model was trained with baseline image data and clinical endpoint data collected from a training cohort of individuals, each individual having the medical disorder.

3. The method as in claim 2, wherein the clinical endpoint data includes biomedical images acquired at the clinical endpoint.

4. The method as in claim 1, wherein the trained and validated predictive model was trained with biomedical image data acquired during the medical disorder progression.

5. The method as in claim 4, wherein the prediction model is further trained with clinical data or genetic data.

6. The method as in claim 1, wherein the trained and validated predictive model has been assessed utilizing baseline biomedical images of an assessment cohort of subjects.

7. The method as in claim 1, wherein the trained and validated predictive model incorporates a deep neural network (DNN), a convolutional neural network (CNN), a kernel ridge regression (KRR), or a gradient-boosted random forest technique.

8. The method as in claim 1, wherein the trained and validated predictive model was trained unsupervised.

9. The method as in claim 1, wherein the trained and validated predictive model was trained utilizing attention that focus the on specific target structures within the baseline biomedical images.

10. The method as in claim 1, wherein the medical disorder is a physical condition, a mental condition, or a risk of a physical or mental condition that deviates from the norm.

11. The method as in claim 1, wherein the results of the predictive model of each subject of the cohort are utilized as an individualized control for the subject using paired statistical tests.

12. The method as in claim 1, wherein the results of the predictive model of each subject are statistically combined together to formulate the control arm.

13. The method as in claim 1, wherein the collection of predicted disorder progression of each subject of the cohort is utilized within a control arm in a clinical experiment that assesses the ability of the experimental treatment to ameliorate the medical disorder, wherein the control arm also includes experimental data of subject receiving a placebo or standard of care alone.

14. The method as in claim 13, wherein the number of subjects within the control arm is less than 50% of the total number of subjects in the clinical experiment.

15. The method as in claim 14, wherein the number of subjects within the control arm is 5%, 10%, 15%, 20%, 25%, 30%, 35%, 40%, or 45% of the total number of subjects in the clinical experiment.

16. The method as in claim 1, wherein the baseline biomedical images are obtained via magnetic resonance imaging (MRI), X-ray, fluoroscopic imaging, computed tomography (CT), ultrasound sonography (US), or positron emission tomography (PET).

17. The method as in claim 1, wherein voxels within each of the baseline biomedical images are weighted relative to other voxels within its image.

18. The method as in claim 1, wherein the predictive model predicts a clinical endpoint, at least one biomedical image depicting medical disorder progression, or the presence at least one biomarker indicating medical disorder progression.

19. The method as in claim 1, wherein the treatment is administration of a drug, performing a surgical procedure, implanting a prosthetic implant, or administration of a vaccine.

* * * * *